US009061070B2

(12) United States Patent
Belmares et al.

(10) Patent No.: US 9,061,070 B2
(45) Date of Patent: Jun. 23, 2015

(54) TREATING STROKE AND OTHER DISEASES WITHOUT INHIBITING N-TYPE CALCIUM CHANNELS

(75) Inventors: Michael P. Belmares, San Jose, CA (US); Jonathan David Garman, San Jose, CA (US); Peter S. Lu, Palo Alto, CA (US); Michael W. Salter, Toronto (CA); Michael Tymianski, Toronto (CA)

(73) Assignee: NoNO, Inc. (CA)

( * ) Notice: Subject to any disclaimer, the term of this patent is extended or adjusted under 35 U.S.C. 154(b) by 22 days.

(21) Appl. No.: 13/620,438

(22) Filed: Sep. 14, 2012

(65) Prior Publication Data

US 2013/0172230 A1    Jul. 4, 2013

Related U.S. Application Data

(62) Division of application No. 12/040,851, filed on Feb. 29, 2008, now Pat. No. 8,288,345.

(60) Provisional application No. 60/904,507, filed on Mar. 2, 2007.

(51) Int. Cl.
| | |
|---|---|
| *A61K 38/02* | (2006.01) |
| *C07K 14/00* | (2006.01) |
| *A61K 47/48* | (2006.01) |
| *C07K 14/705* | (2006.01) |
| *C07K 7/06* | (2006.01) |
| *A61K 38/00* | (2006.01) |

(52) U.S. Cl.
CPC ............ *A61K 47/48246* (2013.01); *A61K 38/00* (2013.01); *C07K 14/70571* (2013.01); *C07K 2319/10* (2013.01); *C07K 7/06* (2013.01); *A61K 47/48315* (2013.01)

(58) Field of Classification Search
None
See application file for complete search history.

(56) References Cited

U.S. PATENT DOCUMENTS

| | | | | |
|---|---|---|---|---|
| 6,001,575 | A * | 12/1999 | Huganir et al. | 435/6.16 |
| 6,399,075 | B1 * | 6/2002 | Howley et al. | 424/204.1 |
| 7,510,824 | B2 * | 3/2009 | Tymianski | 435/4 |
| 8,288,345 | B2 | 10/2012 | Belmares et al. | |

FOREIGN PATENT DOCUMENTS

| | | |
|---|---|---|
| WO | WO 01/49832 A2 | 7/2001 |
| WO | WO 03/076561 A2 | 9/2003 |
| WO | WO 2005/035562 A1 | 4/2005 |
| WO | WO 2006/084179 A2 | 8/2006 |

OTHER PUBLICATIONS

Aarts M M et al., "Uncoupling of NMDAR Signaling from Neurotoxicity by Tat-Fusion Peptides," Program No. 245.2, *Neuroscience Meeting Planner*, Orlando, FL: Society for Neuroscience, 2002. Online.
Aarts Michelle et al., "Treatment of ischemic brain damage by perturbing NMDA receptor-PSD-95 protein interactions," *Science*, American Association for the Advancement of Science, 298(5594):846-850 (2002). ISSN: 0036-8075.
European Search Opinion of Jul. 10, 2010 for application EP 08 72 6313.
Hsu Chun et al., "Perturbing NMDA Receptor-PSD-95 Protein Interactions Prevents Selective Loss of Nitric Oxide Synthase (NOS) Containing Neuron in Rat Gastric Myenteric Plexus," *Digestive Disease Week Meeting/107th Annual Meeting of The American-Gastroenterological-Association*, 130(4.2):A30 (2006). Abstract. ISSN: 0016-5085.
*Journal of Neuroscience*, 27(37):9901-991(2007). ISSN: 0270-6474.
Liu Y et al., "Uncoupling NMDA Receptor-PSD-95 Protein Interactions Reduces Infarction in Focal Cerebral Ischemia in Rats," Program No. 245.3, *Neuroscience Meeting Planner*, Orlando, FL: Society for Neuroscience, 2002. Online.
PCT Search Report of Aug. 13, 2008 for application PCT/US2008/02754.
PCT Written Opinion of Aug. 13, 2008 for application PCT/US2008/02754.
Supplementary European Search Report of May 7, 2010 for application EP 08 72 6313.
Tyagi, et al. "Internalization of HIV-I Tat Requires Cell Surface Heparan Sulfate Proteoglycans" J Biological Chemistry, vol. 276(5):3254-3261 (2001).
U.S. Appl. No. 12/040,851, Requirement for Restriction/Election mailed Sep. 17, 2009.
U.S. Appl. No. 12/040,851, Requirement for Restriction/Election mailed Jan. 22, 2010.
U.S. Appl. No. 12/040,851, Non-Final Rejection mailed Jun. 9, 2010.
U.S. Appl. No. 12/040,851, Final Rejection mailed Jan. 20, 2011.
U.S. Appl. No. 12/040,851, Non-Final Rejection mailed Oct. 5, 2011.
U.S. Appl. No. 12/040,851, Notice of Allowance and Examiner Initiated Interview Summary mailed Jun. 8, 2012.

* cited by examiner

*Primary Examiner* — Michael Pak
(74) *Attorney, Agent, or Firm* — Alston & Bird LLP

(57) ABSTRACT

The invention provides methods for treating stroke and compositions for use in the same. The methods employ a chimeric peptide of an active peptide and an internalization peptide. The internalization peptide is a tat variant that promotes uptake of itself and a linked active peptide into a cell without substantial binding to N-type calcium channels. Use of the tat variant allows treating of stroke free of certain side effects associated with binding to N-type calcium channels. Tat variant peptides can also be linked to other active agent for use in treating other diseases.

7 Claims, 11 Drawing Sheets

Figure 1A:

| Cat. # | TARGET | BATCH* | SPP. | n= | CONC. | ÷% INHIBITION |
|---|---|---|---|---|---|---|
| 200510 | Adenosine $A_1$ | 151494 | hum | 2 | 10 µM | -8 |
| 200610 | Adenosine $A_{2A}$ | 151495 | hum | 2 | 10 µM | 0 |
| 200720 | Adenosine $A_3$ | 151503 | hum | 2 | 10 µM | -22 |
| 203500 | Adrenergic $\alpha_1$, Non-Selective | 151722 | rat | 2 | 10 µM | -19 |
| 203900 | Adrenergic $\alpha_2$, Non-Selective | 151551 | rat | 2 | 10 µM | -5 |
| 204010 | Adrenergic $\beta_1$ | 151527 | hum | 2 | 10 µM | 8 |
| 205000 | Anaphylatoxin C5a | 151609 | hum | 2 | 10 µM | 15 |
| 210110 | Angiotensin $AT_2$ | 151781 | hum | 2 | 10 µM | 12 |
| 226700 | Benzodiazepine, Peripheral | 151814 | rat | 2 | 10 µM | -17 |
| 212610 | Bradykinin $B_2$ | 151530 | hum | 2 | 10 µM | -7 |
| 214510 | Calcium Channel L-Type, Benzothiazepine | 151496 | rat | 2 | 10 µM | 6 |
| 214600 | Calcium Channel L-Type, Dihydropyridine | 151497 | rat | 2 | 10 µM | 5 |
| 215000 | Calcium Channel L-Type, Phenylalkylamine | 151498 | rat | 2 | 10 µM | 4 |
| ♦ 216000 | Calcium Channel N-Type | 151744 | rat | 2 | 10 µM | 108 |
| 217500 | Chemokine CCR1 | 151506 | hum | 2 | 10 µM | -15 |
| ♦ 244500 | Chemokine CXCR2 (IL-8$R_B$) | 152328 | hum | 2 | 10 µM | 77 |
| 218010 | Cholecystokinin $CCK_1$ ($CCK_A$) | 152108 | hum | 2 | 10 µM | -11 |
| 219100 | Colchicine | 151615 | rat | 2 | 10 µM | -10 |
| 219500 | Dopamine $D_1$ | 151531 | hum | 2 | 10 µM | 2 |
| 219700 | Dopamine $D_{2S}$ | 151533 | hum | 2 | 10 µM | 1 |
| 224010 | Endothelin $ET_A$ | 151508 | hum | 2 | 10 µM | 1 |
| 226500 | $GABA_A$, Agonist Site | 151572 | rat | 2 | 10 µM | 2 |
| 226600 | $GABA_A$, Benzodiazepine, Central | 152561 | rat | 2 | 10 µM | 12 |
| 226810 | $GABA_A$, Chloride Channel, TBOB | 151537 | rat | 2 | 10 µM | 4 |
| 228510 | $GABA_B$, Non-Selective | 151952 | rat | 2 | 10 µM | 0 |
| 228600 | $GABA_{B1A}$ | 151853 | hum | 2 | 10 µM | -11 |
| 228700 | $GABA_{B1B}$ | 151575 | hum | 2 | 10 µM | 27 |
| 231600 | Galanin GAL2 | 152193 | hum | 2 | 10 µM | -22 |
| 232600 | Glutamate, AMPA | 151576 | rat | 2 | 10 µM | -2 |

| Cat. # | TARGET | BATCH* | SPP. | n= | CONC. | †% INHIBITION % |
|---|---|---|---|---|---|---|
| 232700 | Glutamate, Kainate | 151577 | rat | 2 | 10 µM | -12 |
| 232810 | Glutamate, NMDA, Agonism | 151578 | rat | 2 | 10 µM | 6 |
| 232910 | Glutamate, NMDA, Glycine | 151579 | rat | 2 | 10 µM | 10 |
| 233000 | Glutamate, NMDA, Phencyclidine | 151580 | rat | 2 | 10 µM | -21 |
| 234000 | Glutamate, NMDA, Polyamine | 151619 | rat | 2 | 10 µM | 28 |
| 235010 | Glutamate, Non-Selective | 152191 | rat | 2 | 10 µM | 22 |
| 239000 | Glycine, Strychnine-Sensitive | 151620 | rat | 2 | 10 µM | 18 |
| 239610 | Histamine $H_1$ | 151538 | hum | 2 | 10 µM | 2 |
| 239710 | Histamine $H_2$ | 151539 | hum | 2 | 10 µM | 0 |
| 239810 | Histamine $H_3$ | 151540 | hum | 2 | 10 µM | -28 |
| 239900 | Histamine $H_4$ | 151541 | hum | 2 | 10 µM | -11 |
| 241000 | Imidazoline $I_2$, Central | 151581 | rat | 2 | 10 µM | -17 |
| 241100 | Imidazoline $I_2$, Peripheral | 152162 | rat | 2 | 10 µM | 5 |
| 243510 | Interleukin IL-1 | 151547 | mouse | 2 | 10 µM | 3 |
| 243700 | Interleukin IL-2 | 151710 | mouse | 2 | 10 µM | 6 |
| 244100 | Interleukin IL-6 | 151711 | hum | 2 | 10 µM | -10 |
| 252610 | Muscarinic $M_1$ | 151513 | hum | 2 | 10 µM | 8 |
| 252710 | Muscarinic $M_2$ | 151514 | hum | 2 | 10 µM | 4 |
| 252810 | Muscarinic $M_3$ | 151515 | hum | 2 | 10 µM | -25 |
| 257010 | Neuropeptide Y $Y_1$ | 151516 | hum | 2 | 10 µM | 0 |
| 257110 | Neuropeptide Y $Y_2$ | 151517 | hum | 2 | 10 µM | 6 |
| 258010 | Neurotensin $NT_1$ | 152160 | hum | 2 | 10 µM | 28 |
| 260110 | Opiate δ (OP1, DOP) | 151542 | hum | 2 | 10 µM | -4 |
| 260210 | Opiate κ (OP2, KOP) | 151543 | hum | 2 | 10 µM | 5 |
| 260410 | Opiate µ (OP3, MOP) | 151544 | hum | 2 | 10 µM | 4 |
| 260600 | Orphanin $ORL_1$ | 152161 | hum | 2 | 10 µM | 43 |
| 265800 | Potassium Channel [$SK_{CA}$] | 151632 | rat | 2 | 10 µM | 17 |
| 265900 | Potassium Channel HERG | 151518 | hum | 2 | 10 µM | 7 |
| 271110 | Serotonin (5-Hydroxytryptamine) 5-$HT_{1A}$ | 151594 | hum | 2 | 10 µM | -12 |
| 271650 | Serotonin (5-Hydroxytryptamine) 5-$HT_{2A}$ | 151502 | hum | 2 | 10 µM | 1 |

Fig. 1B

| Cat. # | TARGET | BATCH* | SPP. | n= | CONC. | % | % INHIBITION -100 -50 0 50 100 |
|---|---|---|---|---|---|---|---|
| 271910 | Serotonin (5-Hydroxytryptamine) 5-HT$_3$ | 151598 | hum | 2 | 10 µM | -4 | |
| 272100 | Serotonin (5-Hydroxytryptamine) 5-HT$_{5A}$ | 151601 | hum | 2 | 10 µM | -12 | |
| 272200 | Serotonin (5-Hydroxytryptamine) 5-HT$_6$ | 151602 | hum | 2 | 10 µM | -3 | |
| 279510 | Sodium Channel, Site 2 | 151606 | rat | 2 | 10 µM | -2 | |
| 226400 | Transporter, GABA | 151536 | rat | 2 | 10 µM | 6 | |
| 239100 | Transporter, Glycine | 152079 | rat | 2 | 10 µM | -8 | |
| 287010 | Vasoactive Intestinal Peptide VIP$_1$ | 151520 | hum | 2 | 10 µM | -1 | |
| 287520 | Vasopressin V$_{1A}$ | 151649 | hum | 2 | 10 µM | 3 | |

TREATING STROKE AND OTHER DISEASES WITHOUT INHIBITING N-TYPE CALCIUM CHANNELS

CROSS-REFERENCE TO RELATED APPLICATIONS

This application is a divisional of Ser. No. 12/040,851, filed Feb. 29, 2008, which claims the benefit of provisional application 60/904,507, filed Mar. 2, 2007, each incorporated by reference in its entirety for all purposes.

BACKGROUND OF THE INVENTION

Stroke is predicted to affect more than 600,000 people in the United States a year. In a 1999 report, over 167,000 people died from strokes, with a total mortality of 278,000. In 1998, 3.6 billion was paid to just those Medicare beneficiaries that were discharged from short-stay hospitals, not including the long term care for >1,000,000 people that reportedly have functional limitations or difficulty with activities of daily living resulting from stroke (Heart and Stroke Statistical update, American Heart Association, 2002). No therapeutic has been approved to reduce brain damage resulting from stroke through the direct protection neurons from death.

Stroke is characterized by neuronal cell death in areas of ischemia, brain hemorrhage and/or trauma. Cell death is triggered by glutamate over-excitation of neurons, leading to increased intracellular $Ca^{2+}$ and increased nitric oxide due to an increase in nNOS (neuronal nitric oxide synthase) activity.

Glutamate is the main excitatory neurotransmitter in the central nervous system (CNS) and mediates neurotransmission across most excitatory synapses. Three classes of glutamate-gated ion channel receptors (N-methyl-D-aspartate (NMDA), alpha-amino-3-hydroxy-5-methylisoxazole-4-propionic acid (AMPA) and Kainate) transduce the postsynaptic signal. Of these, NMDA receptors (NMDAR) are responsible for a significant portion of the excitotoxicity of glutamate. NMDA receptors are complex having an NR1 subunit and one or more NR2 subunits (2A, 2B, 2C or 2D) (see, e.g., McDain, C. and Caner, M. (1994) Physiol. Rev. 74:723-760), and less commonly, an NR3 subunit (Chatterton et al. (2002) Nature 415:793-798). The NR1 subunits have been shown to bind glycine, whereas NR2 subunits bind glutamate. Both glycine and glutamate binding are required to open the ion channel and allow calcium entry into the cell. The four NR2 receptor subunits appear to determine the pharmacology and properties of NMDA receptors, with further contributions from alternative splicing of the NR1 subunit (Kornau et al. (1995) Science 269:1737-40). Whereas NR1 and NR2A subunits are ubiquitously expressed in the brain, NR2B expression is restricted to the forebrain, NR2c to the cerebellum, and NR2D is rare compared to the other types.

Because of the key role of NMDA receptors in the excitotoxicity response, they have been considered as targets for therapeutics. Compounds have been developed that target the ion channel (ketamine, phencyclidine, PCP, MK801, amantadine), the outer channel (magnesium), the glycine binding site on NR1 subunits, the glutamate binding site on NR2 subunits, and specific sites on NR2 subunits (Zinc-NR2A; Ifenprodil, Traxoprodil-NR2B). Among these, the non-selective antagonists of NMDA receptor have been the most neuroprotective agents in animal models of stroke. However, clinical trials with these drugs in stroke and traumatic brain injury have so far failed, generally as a result of severe side effects such as hallucination and even coma.

Postsynaptic density-95 protein (PSD-95) has been reported to couple NMDARs in pathways mediating excitotoxicity and ischemic brain damage (Aarts et al., Science 298, 846-850 (2002)). This coupling was disrupted by transducing neurons with peptides from the C-terminus of NMDAR 2B that bind to PSD-95 fused to a standard tat internalization peptide. This treatment attenuated downstream NMDAR signaling without inhibiting NMDAR activity, protected cultured cortical neurons from excitotoxic insults and reduced cerebral infarction volume in rats subjected to transient focal cerebral ischemia.

BRIEF SUMMARY OF THE INVENTION

The invention provides an isolated chimeric peptide or peptidomimetic thereof, wherein the chimeric peptide comprises an active peptide that inhibits binding of PSD-95 to an NMDA receptor and an internalization peptide that promotes uptake of the chimeric peptide into cells and has reduced capacity to bind to an N-type calcium channel relative to the tat peptide YGRKKRRQRRR (SEQ ID NO:1). Optionally, the internalization peptide is a variant of the tat peptide. Optionally, the active peptide has an amino acid sequence consisting of 3-25 amino acids from the C-terminus of an NMDA receptor or a PDZ domain 1 and/or 2 from a PSD-95 receptor. Optionally, the active peptide has an amino acid sequence comprising T/SXV/L (SEQ ID NO:14) and the internalization peptide has an amino acid sequence comprising XGRKKRRQRRR (SEQ ID NO:2), wherein X is an amino acid other than Y or nothing. Optionally, X is F (SEQ ID NO:135). Optionally, X is nothing (SEQ ID NO:136). Optionally the internalization peptide consists of GRKKRRQRRRP (SEQ ID NO:3). Optionally, the chimeric peptide has an amino acid sequence consisting of GRKKRRQRRRKLSSIESDV (SEQ ID NO:4).

Optionally, the active peptide has an amino acid sequence comprising [E/D/N/Q]-[S/T]-[D/E/Q/N]-[V/L] (SEQ ID NO:5). Optionally, the active peptide comprises an amino acid sequence selected from the group consisting of ESDV (SEQ ID NO:6), ESEV (SEQ ID NO:7), ETDV (SEQ ID NO:8), ETEV (SEQ ID NO:9), DTDV (SEQ ID NO:10), DTEV (SEQ ID NO:11). Optionally, the active peptide has an amino acid sequence comprising KLSSIESDV (SEQ ID NO:12). Optionally, the active peptide has an amino acid sequence comprising KLSSIETDV (SEQ ID NO:13). Optionally, the chimeric peptide has an amino acid sequence comprising FGRKKRRQRRRKLSSIESDV (SEQ ID NO:19) or FGRKKRRQRRRKLSSIETDV (SEQ ID NO:16). Optionally, the chimeric peptide has an amino acid sequence consisting of FGRKKRRQRRRKLSSIESDV (SEQ ID NO:19) or FGRKKRRQRRRKLSSIETDV (SEQ ID NO:16). Optionally, the chimeric peptide has a Kd greater than 10 nM for an N-type calcium channel.

The invention further provides a pharmaceutical composition comprising an isolated chimeric peptide or peptidomimetic thereof as described above and a pharmaceutically acceptable carrier.

The invention further provides a method of treating the damaging effect of stroke in a patient having or at risk of stroke or other injury to the CNS, comprising administering to the patient an effective amount of a chimeric peptide or peptidomimetic thereof. The chimeric peptide comprises an active peptide having an amino acid sequence comprising T/SXV/L (SEQ ID NO:14) and an internalization peptide having an amino acid sequence comprising XGRKKRRQRRR (SEQ ID NO:2), wherein X is an amino acid other than Y. Optionally, X is F (SEQ ID NO:135). Optionally, X is nothing (SEQ ID NO:136). Optionally, the internalization peptide consists of GRKKRRQRRRPQ (SEQ ID NO:15). Optionally, the chimeric peptide has an amino acid sequence comprising GRKKRRQRRRKLSSIESDV (SEQ ID NO:4). Optionally, the active peptide has an amino acid sequence comprising [E/D/N/Q]-[S/THD/E/Q/NMV/L] (SEQ ID NO:5). Optionally, the active peptide comprises an amino acid sequence selected from the group consisting of ESDV (SEQ ID NO:6), ESEV (SEQ ID NO:7), ETDV (SEQ ID NO:8), ETEV (SEQ ID NO:9), DTDV (SEQ ID NO:10), DTEV (SEQ ID NO:11). Optionally, the active peptide has an amino acid sequence comprising KLSSIESDV (SEQ ID NO:12). Optionally, the active peptide has an amino acid sequence comprising KLSSIETDV (SEQ ID NO:13). Optionally, the chimeric peptide has an amino acid sequence comprising FGRKKRRQRRRKLSSIESDV (SEQ ID NO:19) or FGRKKRRQRRRKLSSIETDV (SEQ ID NO:16). Optionally, the chimeric peptide has an amino acid sequence consisting of FGRKKRRQRRRKLSSIESDV (SEQ ID NO:19) or FGRKKRRQRRRKLSSIETDV (SEQ ID NO:16). Optionally, the effective dosage is a single dose of 0.05 to 500 mg, optionally 0.1 to 100 mg, 0.5 to 50 mg, or 1-20 mg of the peptide or peptidomimetic. Optionally, the patient has ischemic stroke. Optionally, the patient has hemorrhagic stroke.

Optionally, the patient has above normal susceptibility to side effects mediated by N-type calcium channels. Optionally, the patient has normal or below normal blood pressure. The invention further provides a method of assessing potential side effects of an internalization peptide. The method involves providing an internalization peptide that promotes uptake of an active peptide that inhibits binding of PSD-95 to an NMDA receptor into a cell; and determining binding of the internalization peptide to an N-type calcium channel. The extent of binding being an indicator of potential side effects in clinical use of the internalization peptide. Optionally, the internalization peptide is provided by screening a test peptide to determine whether the test peptide promotes uptake of the active peptide.

The invention further provides an isolated chimeric agent comprising an active agent and an internalization peptide that promotes uptake of the chimeric agent into cells. The internalization peptide is a variant of the tat peptide YGRKKRRQRRR (SEQ ID NO:1) that has reduced capacity to bind to an N-type calcium channel relative to the tat peptide. Optionally, the active agent is an active agent shown in Table 5. Optionally, the internalization peptide has an amino acid sequence comprising XGRKKRRQRRR (SEQ ID NO:2), wherein X is an amino acid other than Y, or nothing. Optionally, X is F (SEQ ID NO:135). Optionally, X is nothing (SEQ ID NO:136). Optionally, the internalization peptide consists of GRKKRRQRRRP (SEQ ID NO:3). Optionally, the chimeric agent has a kD greater than 10 nM for an N-type calcium channel.

The invention further provides a pharmaceutical composition comprising an isolated chimeric agent as described above and a pharmaceutically acceptable carrier.

The invention further provides an internalization peptide having an amino acid sequence comprising XGRKKRRQRRR (SEQ ID NO:2), wherein X is an amino acid other than Y or nothing. Optionally, X is F (SEQ ID NO:135). Optionally, X is nothing (SEQ ID NO:136). Optionally, the internalization peptide consists of GRKKRRQRRRP (SEQ ID NO:3). Optionally, the internalization peptide has a Kd greater than 10 nM for an N-type calcium channel blocking agent.

The invention further provides in a method of facilitating uptake of an active agent into a cell comprising contacting the cell with the active agent linked to an internalization peptide, the improvement wherein the internalization peptide is screened to determine its capacity to bind to an N-type calcium channel.

The invention further provides in a chimeric agent comprising an internalization peptide linked to an active agent, the improvement wherein the internalization peptide has an amino acid sequence comprising XGRKKRRQRRR (SEQ ID NO:2), wherein X is an amino acid other than Y, or nothing.

The invention further provides in a method of treating a neurological disease, comprising administering an active agent to a patient having or susceptible to the disease an effective amount of an active agent having pharmaceutical activity against the disease, the improvement wherein the active agent is linked to a tat variant peptide having an amino acid sequence comprising XGRKKRRQRRR (SEQ ID NO:2), wherein X is an amino acid other than Y, or nothing.

The invention further provides in a method of treating a disease with an active agent having an intracellular activity effective to treat the disease, comprising administering an effective amount of the active agent to a patient having or susceptible to the disease, the improvement wherein the active agent is linked to a tat variant peptide having an amino acid sequence comprising XGRKKRRQRRR (SEQ ID NO:2), wherein X is an amino acid other than Y, or nothing.

BRIEF DESCRIPTION OF THE DRAWINGS

FIGS. 1A, B, C: Results of a receptor binding/inhibition study assessing the ability of the peptide YGRKKRRQRRRKLSSIESDV (SEQ ID NO:17) to inhibit binding of various radiolabeled ligands to cellular receptors.

FIG. 5A shows the effect of Tat-NR2B9c (100 µM) and ω-conotoxin (1 µM) on calcium current in cultured DGR neurons. FIG. 5B shows the nifedipine inhibition of DRG calcium current in the presence of Tat-NR2B9c (100 µM intracellular).

DETAILED DESCRIPTION OF THE INVENTION

I. Definitions

Figure 2:
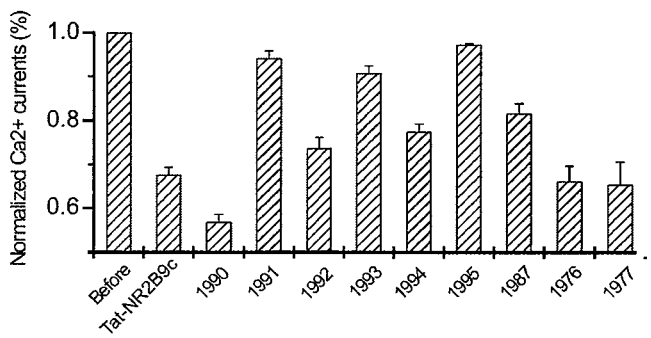
FIG. 2: Effect of applying the various peptides on the amplitude of N-type calcium currents (upper) or whole cell currents (lower) in DRG neurons.
Figure 2:
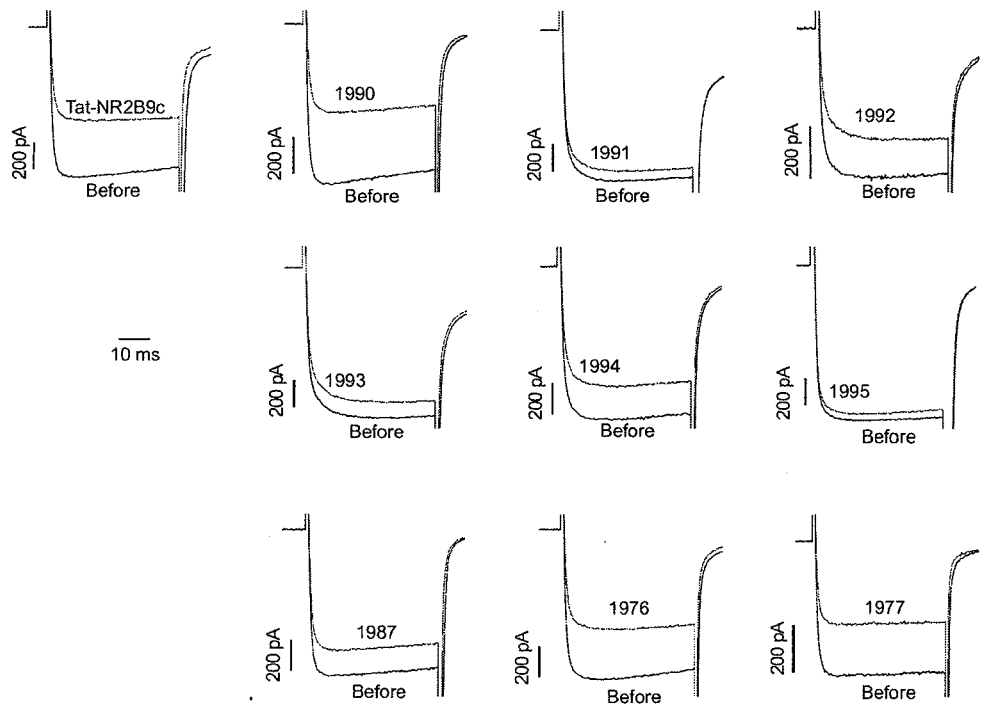

A "chimeric peptide" means a peptide having two component peptides not naturally associated with one another joined to one another as a fusion protein or by chemical linkage.

A "fusion polypeptide" refers to a composite polypeptide, i.e., a single contiguous amino acid sequence, made up of two (or more) distinct, heterologous polypeptides which are not normally fused together in a single amino acid sequence.

The term "PDZ domain" refers to a modular protein domain of about 90 amino acids, characterized by significant sequence identity (e.g., at least 60%) to the brain synaptic protein PSD-95, the *Drosophila* septate junction protein Discs-Large (DLG), and the epithelial tight junction protein ZO1 (ZO1). PDZ domains are also known as Discs-Large homology repeats ("DHRs") and GLGF repeats. PDZ domains generally appear to maintain a core consensus sequence (Doyle, D. A., 1996, *Cell* 85: 1067-76). Exemplary PDZ domain-containing proteins and PDZ domain sequences disclosed in U.S. application Ser. No. 10/714,537, which is herein incorporated by reference in its entirety.

The term "PL protein" or "PDZ Ligand protein" refers to a naturally occurring protein that forms a molecular complex with a PDZ-domain, or to a protein whose carboxy-terminus, when expressed separately from the full length protein (e.g., as a peptide fragment of 3-25 residues, e.g. 3, 4, 5, 8, 9, 10, 12, 14 or 16 residues), forms such a molecular complex. The molecular complex can be observed in vitro using the "A assay" or "G assay" described, e.g., in U.S. application Ser. No. 10/714,537, or in vivo.

The term "NMDA receptor," or "NMDAR," refers to a membrane associated protein that is known to interact with NMDA. The term thus includes the various subunit forms described in the Background Section. Such receptors can be human or non-human (e.g., mouse, rat, rabbit, monkey).

A "PL motif" refers to the amino acid sequence of the C-terminus of a PL protein (e.g., the C-terminal 3, 4, 5, 6, 7, 8, 9, 10, 12, 14, 16, 20 or 25 contiguous residues) ("C-terminal PL sequence") or to an internal sequence known to bind a PDZ domain ("internal PL sequence").

A "PL peptide" is a peptide of comprising or consisting of, or otherwise based on, a PL motif that specifically binds to a PDZ domain.

The terms "isolated" or "purified" means that the object species (e.g., a peptide) has been purified from contaminants that are present in a sample, such as a sample obtained from natural sources that contain the object species. If an object species is isolated or purified it is the predominant macromolecular (e.g., polypeptide) species present in a sample (i.e., on a molar basis it is more abundant than any other individual species in the composition), and preferably the object species comprises at least about 50 percent (on a molar basis) of all macromolecular species present. Generally, an isolated, purified or substantially pure composition comprises more than 80 to 90 percent of all macromolecular species present in a composition. Most preferably, the object species is purified to essential homogeneity (i.e., contaminant species cannot be detected in the composition by conventional detection methods), wherein the composition consists essentially of a single macromolecular species. The term isolated or purified does not necessarily exclude the presence of other components intended to act in combination with an isolated species. For example, an internalization peptide can be described as isolated notwithstanding that it is linked to an active peptide.

A "peptidomimetic" refers to a synthetic chemical compound which has substantially the same structural and/or functional characteristics of a peptide consisting of natural amino acids. The peptidomimetic can contain entirely synthetic, non-natural analogues of amino acids, or can be a chimeric molecule of partly natural peptide amino acids and partly non-natural analogs of amino acids. The peptidomimetic can also incorporate any amount of natural amino acid conservative substitutions as long as such substitutions also do not substantially alter the mimetic's structure and/or inhibitory or binding activity. Polypeptide mimetic compositions can contain any combination of nonnatural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. In a peptidomimetic of a chimeric peptide comprising an active peptide and an internalization peptide, either the active moiety or the internalization moiety or both can be a peptidomimetic.

The term "specific binding" refers to binding between two molecules, for example, a ligand and a receptor, characterized by the ability of a molecule (ligand) to associate with another specific molecule (receptor) even in the presence of many other diverse molecules, i.e., to show preferential binding of one molecule for another in a heterogeneous mixture of molecules. Specific binding of a ligand to a receptor is also evidenced by reduced binding of a detectably labeled ligand to the receptor in the presence of excess unlabeled ligand (i.e., a binding competition assay).

Excitotoxicity is the pathological process by which neurons are damaged and killed by the overactivation of receptors for the excitatory neurotransmitter glutamate, such as the NMDA receptors such as NMDAR 2B.

A standard tat internalization peptide comprises the amino acid sequence YGRKKRRQRRR (SEQ ID NO:1).

A variant tat internalization peptide has at least one amino acid deleted substituted, or internally inserted relative to a standard tat peptide.

An active agent is used to describe a compound that has or may have a pharmacological activity. Agents include compounds that are known drugs, compounds for which pharmacological activity has been identified but which are undergoing further therapeutic evaluation, and compounds that are members of collections and libraries that are to be screened for a pharmacological activity. An active peptide is an active agent that is a peptide. An active chimeric agent comprises an active agent linked to an internalization peptide.

A "pharmacological" activity means that an active agent exhibits an activity in a screening system that indicates that the active agent is or may be useful in the prophylaxis or treatment of a disease. The screening system can be in vitro, cellular, animal or human. Agents can be described as having pharmacological activity notwithstanding that further testing may be required to establish actual prophylactic or therapeutic utility in treatment of a disease.

Statistically significant refers to a p-value that is <0.05, preferably <0.01 and most preferably <0.001.

II. General

The invention provides chimeric peptides and peptidomimetics thereof useful for reducing damaging effects of stroke and other neurological conditions mediated at least in part by NMDAR excitotoxicity. The chimeric peptides have at least two components. The first component is an active peptide having an amino acid sequence including or based on the PL motif of a NMDA Receptor 2 subunit (e.g., GenBank accession number 4099612 for NMDA NR2B) (i.e., a PL peptide). Although an understanding of mechanism is not required for practice of the invention, it is believed that such peptides act at least in part by inhibiting interaction between NMDARs with postsynaptic density 95 protein (i.e., PSD-95 inhibitors).

The active peptides may also inhibit interactions between PSD-95 and nNOS and other glutamate receptors (e.g., kainite receptors or AMPA receptors). Unlike glutamate antagonists that have previously failed clinical trials, such peptides can disrupt neurotoxic signaling during ischemia without incurring the negative consequences of loss of other functions of NMDARs. The second component of the chimeric peptide is an internalization peptide that represents a variant of the standard tat peptide fused to NMDAR 2B peptides in previous work.

The use of a variant tat peptide is premised in part on the results described in the present application that a standard tat peptide, particularly when joined to an NMDAR peptide KLSSIESDV (SEQ ID NO:12), binds to N-type calcium channels and inhibits their activity. N-type calcium channels located on presynaptic nerve terminals regulate neurotransmitter release, including that from the spinal terminations of primary afferent nocioceptors. The pharmacological effects of binding to N-type channels have been well characterized in connection with the drug Ziconotide (or Prialt, a synthetic form of the cone snail peptide omega-conotoxin M-VII-A precursor). Binding to N-type calcium channels has been associated with numerous activities, some or all of which may be undesirable in stroke patients. These activities include analgesia much stronger than that induced by morphine, hypotension, decreased levels of consciousness, depression, cognitive impairment, hallucination, elevation of creatine kinase levels, and urinary retention (see, e.g., Brose et al., Clin J Pain 13: 256-259, (1997); Mathur et al., Semin Anesthesia Perioperative Med Pain 19: 67-75,2000, Staats et al., JAMA 291: 63-70,2004, McGuire et al., J Cardiovasc Pharmacol 30: 400-403,1997. The Mayo clinic lists the following side effects observed after treatment with Prialt, which is highly selective for N-type calcium channels.

TABLE 1

| Severity | Incidence | Phenotypes |
| --- | --- | --- |
| Serious | Common | Seeing, hearing, or feeling things that are not there; thoughts of killing oneself. |
| | Less Common | Chest pain; chills; confusion; convulsions; cough; dark-colored urine; dizziness; drowsiness; fainting; fast heartbeat; fever; general feeling of illness; lightheadedness; muscle spasm or jerking of all extremities; muscle stiffness; rapid, shallow breathing; shortness of breath; sneezing; sore throat; stiff neck or back; tightness in chest; troubled breathing; trouble concentration; trouble sleeping; unusual tiredness or weakness; wheezing. |
| | Overdose | Decreased awareness or responsiveness; severe sleepiness; shakiness and unsteady walk; trembling or other problems with muscle control or coordination; uncontrolled eye movements; unsteadiness |
| Moderate | Common | Burning; change in walking and balance; clumsiness or unsteadiness; confusion; crawling feelings; diarrhea; dizziness; excessive muscle tone, muscle tension or tightness; fear; feeling of constant movement of self or surroundings; fever; headache; itching; lack or loss of strength; lightheadedness; loss of appetite; nausea; nervousness; numbness; problems with speech or speaking; sensation of spinning; trembling, or other problems with muscle control or coordination; uncontrolled eye movements; urinary retention; vomiting; weight loss. |
| | Less Common | Acid or sour stomach; back pain; bad, unusual or unpleasant (after)taste; belching; bladder pain; bloody or cloudy urine; bruising; cerebrospinal fluid abnormal; change in taste; congestion; constipation; continuing ringing or buzzing or other unexplained noise in ears; crying; decreased awareness or responsiveness; dehydration; depersonalization; depression; difficult, burning or painful urination; difficulty in moving; difficulty seeing at night; double vision; dry mouth; dry skin; dryness or soreness of throat; dysphoria; euphoria; fainting; fast or irregular heartbeat; feeling that others can hear your thoughts, are watching you, or can control your behavior; frequent urge to urinate; hearing loss; heartburn; hoarseness; hostility; increased sensitivity of eyes to sunlight; increased sensitivity to pain or touch; indigestion; loss of bladder control; loss of memory or problems with memory; lung disorder; neck pain; nerve pain; pain in joints; pale skin; pounding in ears; quick to react or overreact emotionally; rapidly changing moods; red, scaly, swollen or peeling areas of skin; redness or pain at catheter site; runny nose; severe muscle stiffness; sleeplessness; slow or fast heartbeat; stomach discomfort, upset or pain; sweating; swelling or redness in joints; tender, swollen glands in neck; trouble in swallowing; unusual bleeding or bruising; unusual tiredness or weakness; voice changes; warmth on skin; weakness or heaviness in legs. |

The present chimeric peptides and peptidomimetics have reduced or eliminated binding to and inhibiting of N-type calcium channels compared with Tat-NR2B9c and thus avoid the large number of side effects observed with highly specific inhibitors of the N-type calcium channel, including severe psychiatric side effects. The reduction in side effects results in an increase in the therapeutic index for treatment of humans of the present chimeric peptide and peptidomimetics relative to Tat-NR2B9c.

The present inventors have further found that binding to N-type calcium channels can be avoided by uses of variants of the standard tat sequence. The combination of a tat variant and an active peptide based on or including the C-terminus of NMDAR 2B or other subtype allows treatment of stroke with reduced side effects due to inhibition of N-type calcium channels.

III. Active Peptides

Active peptides useful in the invention inhibit interaction between PDZ domains 1 and 2 of postsynaptic density-95 protein (PSD-95)(human amino acid sequence provided by Stathakism, Genomics 44(1):71-82 (1997)) and the C-terminal PL sequence of one or more NMDA Receptor 2 subunits including the NR2B subunit of the neuronal N-methyl-D-aspartate receptor (Mandich et al., Genomics 22, 216-8 (1994)). NMDAR2B has GenBank ID 4099612, a C-terminal 20 amino acids FNGSSNGHVYEKLSSIESDV (SEQ ID NO:24) and a PL motif ESDV (SEQ ID NO:6). Active peptides preferably inhibit the human forms of PSD-95 and human NMDAR receptors. However, inhibition can also be shown from species variants of the proteins. A list of NMDA and glutamate receptors that can be used appears below:

TABLE 2

NMDA RECEPTORS WITH PL SEQUENCES

| Name | GI or Acc# | C-terminal 20mer sequence | C-terminal 4mer sequence | internal PL? | PL ID |
|---|---|---|---|---|---|
| NMDAR1 | 307302 | HPTDITGPLNLSDPSVSTVV (SEQ ID NO: 25) | STVV (SEQ ID NO: 39) | X | AA216 |
| NMDAR1-1 | 292282 | HPTDITGPLNLSDPSVSTVV (SEQ ID NO: 25) | STVV (SEQ ID NO: 39) | X | AA216 |
| NMDAR1-4 | 472845 | HPTDITGPLNLSDPSVSTVV (SEQ ID NO: 25) | STVV (SEQ ID NO: 39) | X | AA216 |
| NMDAR1-3b | 2343286 | HPTDITGPLNLSDPSVSTVV (SEQ ID NO: 25) | STVV (SEQ ID NO: 39) | X | AA216 |
| NMDAR1-4b | 2343288 | HPTDITGPLNLSDPSVSTVV (SEQ ID NO: 25) | STVV (SEQ ID NO: 39) | X | AA216 |
| NMDAR1-2 | 11038634 | RRAIEREEGQLQLCSRHRES (SEQ ID NO: 26) | HRES (SEQ ID NO: 40) | | |
| NMDAR1-3 | 11038636 | RRAIEREEGQLQLCSRHRES (SEQ ID NO: 26) | HRES (SEQ ID NO: 40) | | |
| NMDAR2C | 6006004 | TQGFPGPCTWRRISSLESEV (SEQ ID NO: 27) | ESEV (SEQ ID NO: 7) | X | AA180 |
| NMDAR3 | 560546 | FNGSSNGHVYEKLSSIESDV (SEQ ID NO: 24) | ESDV (SEQ ID NO: 6) | X | AA34.1 |
| NMDAR3A | 17530176 | AVSRKTELEEYQRTSRTCES (SEQ ID NO: 28) | TCES (SEQ ID NO: 41) | | |
| NMDAR2B | 4099612 | FNGSSNGHVYEKLSSIESDV (SEQ ID NO: 24) | ESDV (SEQ ID NO: 6) | X | |
| NMDAR2A | 558748 | LNSCSNRRVYKKMPSIESDV (SEQ ID NO: 29) | ESDV (SEQ ID NO: 6) | X | AA34.2 |
| NMDAR2D | 4504130 | GGDLGTRRGSAHFSSLESEV (SEQ ID NO: 30) | ESEV (SEQ ID NO: 7) | X | |

TABLE 2-continued

NMDA RECEPTORS WITH PL SEQUENCES

| Name | GI or Acc# | C-terminal 20mer sequence | C-terminal 4mer sequence | internal PL? | PL ID |
|------|------------|---------------------------|--------------------------|--------------|-------|
| Glutamate receptor delta 2 | AF009014 | QPTPTLGLNLGNDPDRGTSIGTSI (SEQ ID NO: 31) | (SEQ ID NO: 42) | X | |
| Glutamate receptor 1 | I28953 | MQSIPCMSHSSGMPLGATGLATGL (SEQ ID NO: 32) | (SEQ ID NO: 43) | X | |
| Glutamate receptor 2 | L20814 | QNFATYKEGYNVYGIESVKISVKI (SEQ ID NO: 33) | (SEQ ID NO: 44) | X | |
| Glutamate receptor 3 | AF167332 | QNYATYREGYNVYGTESVKISVKI (SEQ ID NO: 34) | (SEQ ID NO: 44) | X | |
| Glutamate receptor 4 | U16129 | HTGTAIRQSSGLAVIASDLPSDLP (SEQ ID NO: 35) | (SEQ ID NO: 45) | | |
| Glutamate receptor 5 | U16125 | SFTSILTCHQRRTQRKETVAETVA (SEQ ID NO: 36) | (SEQ ID NO: 46) | X | |
| Glutamate receptor 6 | U16126 | EVINMHTFNDRRLPGKETMAETMA (SEQ ID NO: 37) | (SEQ ID NO: 47) | X | |
| Glutamate receptor 7 | U16127 | RRLPGKDSMACSTSLAPVFPPVFP (SEQ ID NO: 38) | (SEQ ID NO: 48) | | |

Evidence for a role of different NMDAR subtypes in excitotoxicity is provided by e.g., Lynch, J. Pharm. Exp. Therapeutics 300, 717-723 (2002); Kemp, Nature Neurosci. supplement, vol 5 (2002). Some active peptides inhibit interactions between PSD-95 and multiple NMDAR subunits. In such instances, use of the peptide does not necessarily require an understanding of the respective contributions of the different NMDARs to excitotoxicity. Other active peptides are specific for a single NMDAR.

Active peptides include or are based on a PL motif from the C-terminus of any of the above subunits and have an amino acid sequence comprising [S/T]-X-[V/L] (SEQ ID NO:14). This sequence preferably occurs at the C-terminus of the peptides of the invention. Preferred peptides have an amino acid sequence comprising [E/D/N/Q]-[S/T]-[D/E/Q/N]-[V/L] (SEQ ID NO:5) at their C-terminus. Exemplary peptides comprise: ESDV (SEQ ID NO:6), ESEV (SEQ ID NO.:7), ETDV (SEQ ID NO:8), ETEV (SEQ ID NO:9), DTDV (SEQ ID NO:10), and DTEV (SEQ ID NO:11) as the C-terminal amino acids. Two particularly preferred peptides are KLSSIESDV (SEQ ID NO:12), and KLSSIETDV (SEQ ID NO:13). Peptides of the invention without an internalization peptide usually have 3-25 amino acids, peptide lengths (also without an internalization peptide) of 5-10 amino acids, and particularly 9 amino acids are preferred. In some such active peptides, all amino acids are from the C-terminus of an NMDA receptor.

Other active peptides include PDZ domain 1 and/or 2 of PSD-95 or a subfragment of any of these that inhibits interactions between PSD-95 and an NMDA receptor, such as NMDA 2B. Such active peptides comprise at least 50, 60, 70, 80 or 90 amino acids from PDZ domain 1 and/or PDZ domain 2 of PSD-95, which occur within approximately amino acids 65-248 of PSD-95 provided by Stathakism, Genomics 44(1): 71-82 (1997) (human sequence) or NP_031890.1, GI:6681195 (mouse sequence) or corresponding regions of other species variants.

III. Internalization Peptides

Any of the active peptides of the invention can be linked, preferably at its N-terminus, to an internalization peptide that facilitates translocation through the plasma membrane of a cell. Internalization peptides comprise a variant of a standard tat sequence YGRKKRRQRRR (SEQ ID NO:1). Although practice of the invention is not dependent on an understanding of mechanism, it is believed that both capacity to cross membranes and binding to N-type calcium channels are conferred by the unusually high occurrence of positively charged residues Y, R and K in the peptide. Variant peptides for use in the invention should retain ability to facilitate uptake into cells but have reduced capacity to bind N-type calcium channels. Some suitable internalization peptides comprise or consist of an amino acid sequence XGRKKRRQRRR (SEQ ID NO:2), in which X is an amino acid other than Y (e.g., any of the other 19 natural amino acids) or nothing (in which case G is a free N-terminal residue). A preferred tat variant has the N-terminal Y residue substituted with F. Thus, a tat variant comprising or consisting of FGRKKRRQRRR (SEQ ID NO:49) is preferred. Another preferred variant tat internalization peptide consists of GRKKRRQRRR (SEQ ID NO:50). If additional residues flanking XGRKKRRQRRR (SEQ ID NO:2) are present (beside the active peptide) the residues can be for example, natural amino acids flanking this segment from a tat protein, spacer or linker amino acids of a kind typically used to join two peptide domains, e.g., Gly (Ser)$_4$ (SEQ ID NO:134), T G E K P (SEQ ID NO:51), GGRRGGGS (SEQ ID NO:52), or LRQRDGERP (SEQ ID NO:53) (see, e.g., Tang et al. (1996), J. Biol. Chem. 271, 15682-15686; Hennecke et al. (1998), Protein Eng. 11, 405-410)), or can be any other amino acids that do not detectably reduce capacity to confer uptake of the variant without the flanking residues and do not significantly increase inhibition of N-type calcium channels relative to the variant without the flanking residues. Preferably, the number of flanking amino acids other than an active peptide does not exceed ten on either side of XGRKKRRQRRR. (SEQ ID NO:2). Preferably, no flanking amino acids are present, and the internalization peptide is linked at its C-terminus directly to an active peptide.

Other internalization peptides of the invention that can be used to allow uptake of any of the active peptides of the invention for inhibition of PSD-95 interactions without inhibiting N-type calcium channels include those presented in Table 3 below. It is recommended that these internalization peptides be screened to confirm desired uptake and lack of inhibition of N-type calcium channels, as described in the Examples.

The data presented in the examples demonstrate that mutation of the N-terminal tyrosine residue (Y) of Tat-NR2B9c to phenylalanine (F) is sufficient to abrogate inhibition of the N-type calcium channel without reducing the ability of the remainder of the peptide to localize to the site of action for this drug in the brain and reduce the damage following induced stroke in animals models of permanent ischemia. Further, the experiments demonstrate that Tat alone (YGRKKRRQRRR (SEQ ID NO:1)) is sufficient to induce the observed inhibition of the N-type calcium channel, and that different peptides added at the C-terminus have only a mild effect on the inhibition when attached to Tat. Thus, change or removal of the tyrosine at the N-terminus of the Tat sequence is likely to be important to reduction of binding. Mutation of basic amino acid residues near this tyrosine can also result in a reduction of binding to and inhibition of N-type calcium channels. The exemplary sequences in the table below are predicted herein to maintain transport capability without inhibiting N-type calcium channels and thus allow a greater therapeutic index for the treatment of stroke or neurotrauma.

TABLE 3

| Sequence | SEQ ID |
|---|---|
| X-FGRKKRRQRRRKLSSIESDV (F-TatNR2B9c) | SEQ ID NOS: 19, 77, 78, 79 |
| X-GKKKKKQKKKKLSSIESDV | SEQ ID NO: 54, 80, 81, 82 |
| X-RKKRRQRRRKLSSIESDV | SEQ ID NO: 55, 83, 84, 85 |
| X-GAKKRRQRRRKLSSIESDV | SEQ ID NO: 56, 86, 87, 88 |
| X-AKKRRQRRRKLSSIESDV | SEQ ID NO: 57, 89, 90, 91 |
| X-GRKARRQRRRKLSSIESDV | SEQ ID NO: 58, 92, 93, 94 |
| X-RKARRQRRRKLSSIESDV | SEQ ID NO: 59, 95, 96, 97 |
| X-GRKKARQRRRKLSSIESDV | SEQ ID NO: 60, 98, 99, 100 |
| X-RKKARQRRRKLSSIESDV | SEQ ID NO: 61, 101, 102, 103 |
| X-GRKKRRQARRKLSSIESDV | SEQ ID NO: 62, 104, 105, 106 |
| X-RKKRRQARRKLSSIESDV | SEQ ID NO: 63, 107, 108, 109 |
| X-GRKKRRQRARKLSSIESDV | SEQ ID NO: 64, 110, 111, 112 |
| X-RKKRRQRARKLSSIESDV | SEQ ID NO: 65, 113, 114, 115 |
| X-RRPRRPRRPRRKLSSIESDV | SEQ ID NO: 66, 116, 117, 118 |
| X-RRARRARRARRKLSSIESDV | SEQ ID NO: 67, 119, 120, 121 |
| X-RRRARRRARRKLSSIESDV | SEQ ID NO: 68, 122, 123, 124 |
| X-RRRPRRPRRKLSSIESDV | SEQ ID NO: 69, 125, 126, 127 |
| X-RRPRRPRRKLSSIESDV | SEQ ID NO: 70, 128, 129, 130 |
| X-RRARRARRKLSSIESDV | SEQ ID NO: 71, 131, 132, 133 |

X can represent a free amino terminus, a biotin molecule or other capping moiety including, but not limited to, H, acetyl, benzoyl, alkyl group (aliphatic), pyroglutamate, alkyl group with cycloalkyl group at the end, biotin with alkyl spacer, (5,6)—FAM. Chemical coupling of the capping group to the N-terminal peptide can be through an amide chemistry, sulphamide chemistry, sulphone chemistry, alkylation chemistry. In addition, X can also be an amino acid other that tyrosine.

Internalization peptides are usually linked to active peptides as fusion peptides, but can also be joined by chemical linkage. Coupling of the two constituents can be accomplished via a coupling or conjugating agent. Numerous such agents are commercially available and are reviewed by S. S. Wong, Chemistry of Protein Conjugation and Cross-Linking, CRC Press (1991). Some examples of cross-linking reagents include J-succinimidyl 3-(2-pyridyldithio) propionate (SPDP) or N,N'-(1,3-phenylene)bismaleimide; N,N'-ethylene-bis-(iodoacetamide) or other such reagent having 6 to 11 carbon methylene bridges (which relatively specific for sulfhydryl groups); and 1,5-difluoro-2,4-dinitrobenzene (which forms irreversible linkages with amino and tyrosine groups). Other cross-linking reagents include p,p'-difluoro-m,m'-dinitrodiphenylsulfone (which forms irreversible cross-linkages with amino and phenolic groups); dimethyl adipimidate (which is specific for amino groups); phenol-1,4-disulfonyl-chloride (which reacts principally with amino groups); hexamethylenediisocyanate or diisothiocyanate, or azophenyl-p-diisocyanate (which reacts principally with amino groups); glutaraldehyde (which reacts with several different side chains) and disdiazobenzidine (which reacts primarily with tyrosine and histidine).

Peptides such as those just described can optionally be derivatized (e.g., acetylated, phosphorylated and/or glycosylated) to improve the binding affinity of the inhibitor, to improve the ability of the inhibitor to be transported across a cell membrane or to improve stability. As a specific example, for inhibitors in which the third residue from the C-terminus is S or T, this residue can be phosphorylated before use of the peptide.

Peptides of the invention, optionally fused to internalization domains, can be synthesized by solid phase synthesis or recombinant methods. Peptidomimetics can be synthesized using a variety of procedures and methodologies described in the scientific and patent literature, e.g., Organic Syntheses Collective Volumes, Gilman et al. (Eds) John Wiley & Sons, Inc., NY, al-Obeidi (1998) *Mol. Biotechnol.* 9:205-223; Hruby (1997) *Curr. Opin. Chem. Biol.* 1:114-119; Ostergaard (1997) *Mol. Divers.* 3:17-27; Ostresh (1996) *Methods Enzymol.* 267:220-234.

V. N-Type Calcium Channels

N-type calcium channels are hetero-oligomeric complexes consisting of $\alpha_{1B}$-(Cav2.2), $\beta$-, and $\alpha_2$-$\delta$-subunits and sometimes $\gamma$ subunits. The $\alpha_{1B}$-subunit forms the main channel and is encoded by a single gene. There are four $\alpha_2\delta$-subunit genes ($\alpha_2\delta$-1-$\alpha_2\delta$-4) (Snutch et al., Molecular properties of voltage-gated calcium channels. In: Voltage-gated calcium (Zamponi G, ed), pp 61-94. New York: Landes Bioscience, 2005. Catterall, Biochemical studies of $Ca^{2+}$ channels. In: Voltage-Gated Calcium (Zamponi G, ed), pp 48-60. New York: Landes Bioscience, 2005). There is close conservation of N-type calcium channels across species. Thus tat variants can be screened for lack of binding using N-type calcium channels from humans or other species, such as rats.

The am-subunit N-type calcium channel described by Williams et al., 1992 (Science 257 (5068), 389-395 (1992), Genebank Acc No. Q00975, Species: *Homo Sapiens*) and Coppola et al., 1994 (FEBS Lett. 338 (1), 1-5 (1994), Genebank Acc No 055017, Species: *Mus Musculus*) and Dubel et al., 1992 (Proc. Natl. Acad. Sci. U.S.A. 89 (11), 5058-5062 (1992) Genebank Acc No Q02294, Species: *Rattus norvegicus*) including splice variants and fragments thereof having similar calcium channel activity to the intact protein is preferred for screening. Allelic variants and species variants having at least 90% sequence identity with any of the above sequences can also be used. Optionally, the $\alpha_{1B}$ subunit can be used in combination with an alpha2(a-e)/delta, beta1-4, and/or gamma subunit.

VI. Screening Methods

1. Measuring Binding to N-Type Calcium Channels

Internalization peptides can be screened for binding to N-type calcium channels by a competitive binding assay using a labeled peptide known to bind such channels (e.g., Ziconotide). The N-type calcium channel can be provided in purified form or naturally or recombinantly expressed from cells. If provided in purified form, the N-type calcium channel can be immobilized to beads or to a microliter well. The amount of label bound to the calcium channel after incubation with the labeled peptide and internalization peptide under test is inversely related to the capacity of the internalization peptide under test to bind to the calcium channel. The assay can be performed on a high throughput basis in the wells of a microtiter plate. Negative and positive controls can also be included. A negative control can be vehicle. A positive control can be unlabelled form of the peptide known to bind N-type calcium channels. Preferably an internalization peptide has a Kd greater than 10 nM, preferably greater than 100 nM for an N-type calcium channel.

2. Measuring Inhibition of N-Type Calcium Channels

Internalization peptides and chimeric agents comprising an internalization peptide linked to an active agent, such as an active peptide can be screened for their capacity to inhibit ionic currents mediated by N-type calcium channels. Inhibition means a statistically significant reduction in the measured ionic current carried by N-type calcium channels. Such a reduction should be greater than a 20% reduction in measured current, preferably greater than 30% reduction, and more preferably greater than 40% reduction. Inhibition can be determined by performing whole-cell patch clamp recordings in dorsal root ganglion neurons, in which N-type calcium currents are expressed. Cultures of dorsal root ganglions (DRGs) were prepared from Swiss mice at 13-14 days of gestation. In brief, DRG's are dissected and subjected to trypsin digestion for 20 min at 37° C., mechanically dissociated and plated on cover slips coated with poly-D-lysine. They are grown in serum free MEM (Neurobasal MEM, B-27-Gibco Invitrogen Corporation, Carlsbad, Calif.). After 3-5 days, 10 μM FUDR solution is added to inhibit glial proliferation. The cultures are maintained at 37° C. in a humidified 5% $CO_2$ atmosphere and fed twice a week. Whole-cell recording is carried out at room temperature 10-14 days after plating. Electrophysiology recordings: Whole-cell recordings are performed with an Axopatch-1B amplifier (Axon Instruments, Foster City, Calif.) in the voltage-clamp mode. Recording electrodes, with resistances of 3-5 MΩ, are constructed from thin-walled borosilicate glass (1.5 mm diameter; World Precision Instruments, Sarasota, Fla.) using a two-stage puller (PP83; Narishige, Tokyo, Japan). Data are digitized, filtered (2 kHz), and acquired on-line using the programs of pClamp 9 (Axon Instruments). The pipettes are filled with a solution containing (mM): CsCl 110, MgCl2 3, EGTA 10, HEPES 10, MgATP 3, GTP 0.6. The pH is adjusted to 7.2 with CsOH. The bath solution contained (mM): CaCl2 1, BaCl2 10, HEPES 10, TEA-Cl 160, Glucose 10, TTX 0.0002 at pH (NaOH) 7.4. Whole-cell currents are elicited using 40 ms depolarizing pulses to +20 mV from a holding potential of −60 mV, applied every 15 s. To test the use-dependent inhibition, currents are elicited using 10 ms depolarizing pulses to +20 mV from a holding potential of −60 mV, applied every 0.02 s (50 Hz), 0.05 s (20 Hz), 0.1 s (10 Hz) or 15 s (0.07 Hz) respectively.

3. Measuring Internalization Activity

Variants of the tat internalization peptide can be tested for transport activity in an animal. Internalization peptides can be tested alone or when linked to an active agent, such an active peptide, e.g., KLSSIESDV (SEQ ID NO:12). The internalization peptide, optionally linked to an active agent, such as a peptide, is labeled, preferably with a fluorescent label, such as dansyl chloride. The internalization peptide is then injected peripherally into an animal, such as a mouse. Intraperitoneal or intravenous injection is suitable, for example. About an hour after injection, the mice are sacrificed, perfused with fixative solution (3% paraformaldehyde, 0.25% glutaraldehyde, 10% sucrose, 10 U/mL heparin in saline). Brains are then removed, frozen and sections. Sections are analyzed for fluorescence using a confocal microscope. Internalization activity is determined from fluorescence, optionally relative to positive and negative controls. A suitable positive control is the standard tat peptide linked to the same active peptide (if present) as the internalization peptide under test. A suitable negative control is fluorescently labeled active peptide not linked to an internalization peptide. Unlabelled vehicle can also be used as a negative control.

Similar experiments can be performed in cell culture to test tat variants (see US20030050243). A variant fluorescently labeled tat peptide, optionally linked to an active peptide is applied to a cortical neuronal culture. Uptake is determined using fluorescence microscopy over several minutes after application. Increased uptake can be determined relative to positive and negative controls as described for the experiments on uptake in an animal.

4. Measuring Activity in Treating Stroke

The activity of chimeric peptides comprising a internalization peptide linked to an active peptide (or a peptidomimetic of such a chimeric peptide) can be tested in various animal models of stroke. In one such model, in adult male Sprague-Dawley rats subjected to transient middle cerebral artery occlusion (MCAO) for 90 minutes by the intraluminal suture method (36,37). Animals are fasted overnight and injected with atropine sulfate (0.5 mg/kg IP). After 10 minutes anesthesia is induced. Rats are orally intubated, mechanically ventilated, and paralyzed with pancuronium bromide (0.6 mg/kg IV). Body temperature is maintained at 36.5-37.5° C. with a heating lamp. Polyethylene catheters in the femoral artery and vein are used to continuously record blood pressure and to sample blood for gas and pH measurements. Transient MCAO is achieved for 90 min by introducing a poly-L-lysine-coated 3-0 monofilament nylon suture (Harvard Apparatus) into the circle of Willis via the internal carotid artery, effectively occluding the middle cerebral artery. This produces an extensive infarction encompassing the cerebral cortex and basal ganglia. Animals are treated with either a chimeric peptide under test or a negative or positive control. Treatment can be either before or up to one hour after inducing ischemia. A negative control can be vehicle. A positive control can be the Tat-NR2B9c peptide, YGRKKRRQR-RRKLSSIESDV (SEQ ID NO:17), previously shown to be effective. The chimeric peptide is delivered by a single intravenous bolus injection 45 min prior to MCAO (3 nmoles/g). After administering compounds to the animals, infarction volume and/or disability index are determined. Infarction volumes are usually determined 24 hr post treatment but can be determined at a later time such as 3,7,14 or 60 days. Disability index can be monitored over time, e.g., at 2 hr post treatment, 24 hr post treatment, one week and one month post treatment. Chimeric peptides showing a statistically significant reduction in infarction volume and/or disability index relative to control animals not treated with the compounds are identified as having activity useful for practicing the methods of the invention.

Similar experiments can be performed in animal subject to permanent ischemia. Permanent ischemia of the middle cerebral artery pial vessel can be carried out as described by Forder et al., Am J Physiol Heart Circ Physiol 288:H1989-H1996 (2005). In brief, the right ECA is cannulated with PE 10 polyethylene tubing. The skull is exposed via a midline incision, and a 6- to 8-mm cranial window is made over the right somatosensory cortex (2 mm caudal and 5 mm lateral to bregma). The pial arteries are visualized by injecting small boluses (10-20 μL) of the vital dye patent blue violet (10 mMol/L; Sigma) in normal saline, into the ECA. The same three pial arteriolar MCA branches are electrically cauterized and dye injections are repeated to ensure the interruption of flow through the cauterized arterioles. The incision is then closed and the animal returned to its cage and allowed free access to food and water. This permanent ischemia model produces a highly reproducible small infarction limited to the cortex underlying the coagulated terminal pial arteries.

The left middle cerebral artery can be occluded by the intraluminal suture method described by Longa, Stroke 20, 84-91 (1989). In brief, the left common carotid artery (CCA) is exposed through a midline neck incision and is dissected free from surrounding nerves and fascia, from its bifurcation to the base of the skull. The occipital artery branches of the external carotid artery (ECA) are then isolated, and these branches dissected and coagulated. The ECA is dissected further distally and coagulated along with the terminal lingual and maxillary artery branches, which are then divided. The internal carotid artery (ICA) is isolated and separated from the adjacent vagus nerve, and the pterygopalatine artery is ligated close to its origin. The tip of a 4-cm length of 3-0 monofilament nylon suture (Harvard Apparatus) is rounded by burning to achieve a tip diameter of 0.33-0.36 mm and tip length of 0.5-0.6 mm and coated with poly-L-lysine (Belayev et al., 1996). The suture is introduced through the CCA and advanced into the ICA and thence into the circle of Willis (about 18-20 mm from the carotid bifurcation), effectively occluding the middle cerebral artery. The silk suture around the CCA is tightened around the intraluminal nylon suture to secure it and permanently occlude the middle cerebral artery.

5. Cell-Based Screening of Active Peptides

Optionally, active peptides or peptidomimetics thereof can also be screened for capacity to inhibit interactions between PSD-95 and NMDAR 2B using assays described in e.g., US 20050059597. Useful peptides typically have $IC_{50}$ values of less than 50 μM, 25 μM, 10 μM, 0.1 μM or 0.01 μM in such an assay. Preferred peptides typically have an 1050 value of between 0.001-1 and more preferably 0.05-0.5 or 0.05 to 0.1 μM.

VI. Stroke and Related Conditions

A stroke is a condition resulting from impaired blood flow in the CNS regardless of cause. Potential causes include embolism, hemorrhage and thrombosis. Some neuronal cells die immediately as a result of impaired blood flow. These cells release their component molecules including glutamate, which in turn activates NMDA receptors, which raise intracellular calcium levels, and intracellular enzyme levels leading to further neuronal cell death (the excitotoxicity cascade). The death of CNS tissue is referred to as infarction. Infarction Volume (i.e., the volume of dead neuronal cells resulting from stroke in the brain) can be used as an indicator of the extent of pathological damage resulting from stroke. The symptomatic effect depends both on the volume of an infarction and where in the brain it is located. Disability index can be used as a measure of symptomatic damage, such as the Rankin Stroke Outcome Scale (Rankin, Scott Med J; 2:200-15 (1957)) and the Barthel Index. The Rankin Scale is based on assessing directly the global conditions of a patient as follows.

TABLE 4

0 No symptoms at all
1 No significant disability despite symptoms; able to carry out all usual duties and activities.
2 Slight disability; unable to carry out all previous activities but able to look after own affairs without assistance.
3 Moderate disability requiring some help, but able to walk without assistance
4 Moderate to severe disability; unable to walk without assistance and unable to attend to own bodily needs without assistance.
5 Severe disability; bedridden, incontinent, and requiring constant nursing care and attention.

The Barthel Index is based on a series of questions about the patient's ability to carry out 10 basic activities of daily living resulting in a score between 0 and 100, a lower score indicating more disability (Mahoney et al., Maryland State Medical Journal 14:56-61 (1965)).

Alternatively stroke severity/outcomes can be measured using the NIH stroke scale, available at world wide web ninds.nih.gov/doctors/NIH_Stroke_Scale_Booklet.pdf. The scale is based on the ability of a patient to carry out 11 groups of functions that include assessments of the patient's level of consciousness, motor, sensory and language functions.

An ischemic stroke refers more specifically to a type of stroke that caused by blockage of blood flow to the brain. The underlying condition for this type of blockage is most commonly the development of fatty deposits lining the vessel walls. This condition is called atherosclerosis. These fatty deposits can cause two types of obstruction. Cerebral thrombosis refers to a thrombus (blood clot) that develops at the clogged part of the vessel "Cerebral embolism" refers generally to a blood clot that forms at another location in the circulatory system, usually the heart and large arteries of the upper chest and neck. A portion of the blood clot then breaks loose, enters the bloodstream and travels through the brain's blood vessels until it reaches vessels too small to let it pass. A second important cause of embolism is an irregular heartbeat, known as arterial fibrillation. It creates conditions in which clots can form in the heart, dislodge and travel to the brain. Additional potential causes of ischemic stroke are hemorrhage, thrombosis, dissection of an artery or vein, a cardiac arrest, shock of any cause including hemorrhage, and iatrogenic causes such as direct surgical injury to brain blood vessels or vessels leading to the brain or cardiac surgery. Ischemic stroke accounts for about 83 percent of all cases of stroke.

Transient ischemic attacks (TIAs) are minor or warning strokes. In a TIA, conditions indicative of an ischemic stroke are present and the typical stroke warning signs develop. However, the obstruction (blood clot) occurs for a short time and tends to resolve itself through normal mechanisms.

Hemorrhagic stroke accounts for about 17 percent of stroke cases. It results from a weakened vessel that ruptures and bleeds into the surrounding brain. The blood accumulates and compresses the surrounding brain tissue. The two general types of hemorrhagic strokes are intracerebral hemorrhage and subarachnoid hemorrhage. Hemorrhagic stroke result from rupture of a weakened blood vessel ruptures. Potential causes of rupture from a weakened blood vessel include a hypertensive hemorrhage, in which high blood pressure causes a rupture of a blood vessel, or another underlying cause of weakened blood vessels such as a ruptured brain vascular malformation including a brain aneurysm, arteriovenous malformation (AVM) or cavernous malformation. Hemorrhagic strokes can also arise from a hemorrhagic transformation of an ischemic stroke which weakens the blood vessels in the infarct, or a hemorrhage from primary or metastatic tumors in the CNS which contain abnormally weak blood vessels. Hemorrhagic stroke can also arise from iatrogenic causes such as direct surgical injury to a brain blood vessel. An aneurysm is a ballooning of a weakened region of a blood vessel. If left untreated, the aneurysm continues to weaken until it ruptures and bleeds into the brain. An arteriovenous malformation (AVM) is a cluster of abnormally formed blood vessels. A cavernous malformation is a venous abnormality that can cause a hemorrhage from weakened venous structures. Any one of these vessels can rupture, also causing bleeding into the brain. Hemorrhagic stroke can also result from physical trauma. Hemorrhagic stroke in one part of the brain can lead to ischemic stroke in another through shortage of blood lost in the hemorrhagic stroke.

Several other neurological conditions can also result in neurological death through NDMAR-mediated excitotoxicity. These conditions include epilepsy, hypoxia, traumatic injury to the CNS not associated with stroke such as traumatic brain injury and spinal cord injury, Alzheimer's disease and Parkinson's disease.

VII. Methods of Treatment

The chimeric peptides described above or peptidomimetics thereof are used to treat patients with stroke. Treatment is usually initiated as soon as possible after initiation of the stroke. Occasionally, treatment can be initiated at or before onset of stroke in patients known to be at high risk. Risk factors include hypertension, diabetes, family history, smoking, previous stroke, and undergoing surgery. Usually, treatment is first administered within one to 24 hours after initiation of stroke. Often a single dose of chimeric peptide of the invention is sufficient. However, multiple doses can also be administered at intervals of 6-24 hr or greater.

The use of tat variant peptides having reduced capacity to bind to and inhibit N-type calcium channels is particularly useful in patients having above normal susceptibility to side effects resulting from binding to these channels. These include patients have normal (systolic 120-129 mm Hg and diastolic 80-84 mm Hg) or below normal blood pressure. Subnormal blood pressure can arise as a result of blood loss contemporaneously with insult to the CNS (for example, in a patient who experiences traumatic injury in a car accident, or in a patient who incurs blood loss as a result of a fall following stroke).

The response of the patient to the administration of a chimeric peptide or peptidomimetic of the invention can be monitored by determining infarction volume before and at various times after treatment. Early ischemia is detectable using MRI diffusion imaging. Combinations of MRI protocols, including perfusion imaging, can be used to determine tissue at risk and predict infarction volume. The methods preferably achieve a reduction in infarction volume of at least 10, 15, 20, 25, 30, 35, 40, or 50% relative to the mean infarction volume in a population of comparable patients not receiving treatment by the methods of the invention. The response of the patient can also be measured from a disability index determined one day to one week after initiating treatment. The patient preferably shows an improvement (i.e., less disability) in disability index of at least 4, 10, 15, 20, 25, 30, 35, 40, or 50% relative to the mean disability index in a population of comparable patients not receiving treatment by the methods of the invention. The patient preferably scores a zero or one on the Rankin stroke index or over 75 on the Barthel index.

VIII. Pharmaceutical Compositions, Dosages and Routes of Administration

The chimeric peptides or peptidomimetics of the invention can be administered in the form of a pharmaceutical composition. Pharmaceutical compositions are manufactured under GMP conditions. Pharmaceutical compositions can be provided in unit dosage form (i.e., the dosage for a single administration) containing any of the dosages indicated above. Pharmaceutical compositions can be manufactured by means of conventional mixing, dissolving, granulating, dragee-making, levigating, emulsifying, encapsulating, entrapping or lyophilizing processes. In particular, lyophilized chimeric peptides or peptidomimetics of the invention can be used in the formulations and compositions described below.

Pharmaceutical compositions can be formulated in conventional manner using one or more physiologically acceptable carriers, diluents, excipients or auxiliaries that facilitate processing of chimeric peptides or peptidomimetics into preparations which can be used pharmaceutically. Proper formulation is dependent on the route of administration chosen.

Administration can be parenteral, intravenous, oral, subcutaneous, intraarterial, intracranial, intrathecal, intraperitoneal, topical, intranasal or intramuscular. Intravenous administration is preferred.

Pharmaceutical compositions for parenteral administration are preferably sterile and substantially isotonic. For injection, chimeric peptides can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents.

Alternatively the chimeric peptides or peptidomimetics can be in powder form for constitution with a suitable vehicle, e.g., sterile pyrogen-free water, before use.

For transmucosal administration, penetrants appropriate to the barrier to be permeated are used in the formulation. This route of administration can be used to deliver the compounds to the nasal cavity or for sublingual administration.

For oral administration, the chimeric peptides or peptidomimetics can be formulated with pharmaceutically acceptable carriers as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents can be added, such as the cross-linked polyvinylpyrrolidone, agar, or alginic acid or a salt thereof such as sodium alginate. If desired, solid dosage forms can be sugar-coated or enteric-coated using standard techniques. For oral liquid preparations such as, for example, suspensions, elixirs and solutions, suitable carriers, excipients or diluents include water, glycols, oils, alcohols. Additionally, flavoring agents, preservatives, coloring agents and the like can be added.

In addition to the formulations described previously, the chimeric peptides or peptidomimetics can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems can be employed. Liposomes and emulsions can be used to deliver chimeric peptides. Certain organic solvents such as dimethylsulfoxide also can be employed, although usually at the cost of greater toxicity. Additionally, the compounds can be delivered using a sustained-release system, such as semipermeable matrices of solid polymers containing the therapeutic agent.

Sustained-release capsules can, depending on their chemical nature, release the chimeric peptides for a few weeks up to over 100 days. Depending on the chemical nature and the biological stability of the therapeutic reagent, additional strategies for protein stabilization can be employed.

As the chimeric peptides or peptidomimetics of the invention can contain charged side chains or termini, they can be included in any of the above-described formulations as the free acids or bases or as pharmaceutically acceptable salts. Pharmaceutically acceptable salts are those salts which substantially retain the biologic activity of the free bases and which are prepared by reaction with inorganic acids. Pharmaceutical salts tend to be more soluble in aqueous and other protic solvents than are the corresponding free base forms.

The chimeric peptides or peptidomimetics are used in an amount effective to achieve the intended purpose (e.g., reduction of damage effect of the damaging stroke and related conditions). A therapeutically effective amount means an amount of chimeric peptide or peptidomimetics sufficient to significantly reduce the damage resulting from stroke in a population of patients (or animal models) treated with the chimeric peptides or peptidomimetics of the invention relative to the damage in a control population of stroke patients (or animal models) not treated with the chimeric peptides or peptidomimetics of the invention. The amount is also considered therapeutically effective if an individual treated patient achieves an outcome more favorable than the mean outcome (determined by infarction volume or disability index) in a control population of comparable patients not treated by methods of the invention. The amount is also considered therapeutically effective if an individual treated patient shows a disability of two or less on the Rankin scale and 75 or more on the Barthel scale. A dosage is also considered therapeutically effective if a population of treated patients shows a significantly improved (i.e., less disability) distribution of scores on a disability scale than a comparable untreated population, see Lees et at 1, N Engl J Med 2006; 354:588-600. A therapeutically effective regime means a combination of a therapeutically effective dose and a frequency of administration needed to achieve the intended purpose as described above. Usually a single administration is sufficient.

Preferred dosage ranges include 0.001 to 20 vitriol chimeric peptide or peptidomimetic per kg patient body weight, optionally 0.03 to 3 μmol chimeric peptide per kg patient body weight to μmol chimeric peptide per kg patient body weight within 6 hours of stroke. In some methods, 0.1-20 μmol chimeric peptide or peptidomimetic per kg patient body weight within 6 hours are administered. In some methods, 0.1-10 μmol chimeric peptide or peptidomimetic per kg patient body weight is administered within 6 hours, more preferably about 0.3 μmol chimeric peptide per kg patient body weight within 6 hours. In other instances, the dosages range is from 0.005 to 0.5 μmol chimeric peptide or peptidomimetic per kg patient body weight. Dosage per kg body weight can be converted from rats to humans by dividing by 6.2 to compensate for different surface area to mass ratios. Dosages can be converted from units of moles to grams by multiplying by the molar weight of a chimeric peptide or peptidomimetic. Suitable dosages of chimeric peptides or peptidomimetics for use in humans can include 0.001 to 5 mg/kg patient body weight, or more preferably 0.005 to 1 mg/kg patient body weight or 0.05 to 1 mg/kg, or 0.09 to 0.9 mg/kg. In absolute weight for a 75 kg patient, these dosages translate to 0.075-375 mg, 0.375 to 75 mg or 3.75 mg to 75 mg or 6.7 to 67 mg. Rounded to encompass variations in e.g., patient weight, the dosage is usually within 0.05 to 500 mg, preferably 0.1 to 100 mg, 0.5 to 50 mg, or 1-20 mg.

The amount of chimeric peptide or peptidomimetics administered depends on the subject being treated, on the subject's weight, the severity of the affliction, the manner of administration and the judgment of the prescribing physician. The therapy can be repeated intermittently while symptoms detectable or even when they are not detectable. The therapy can be provided alone or in combination with other drugs.

Therapeutically effective dose of the present chimeric peptides or peptidomimetics can provide therapeutic benefit without causing substantial toxicity. Toxicity of the chimeric peptides can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Chimeric peptides or peptidomimetics exhibiting high therapeutic indices are preferred (see, e.g., Fingl et al., 1975, In: *The Pharmacological Basis of Therapeutics*, Ch.1, p. 1).

IX. Screening Methods

The invention further provides methods of screening other internalization peptides to determine whether such peptides bind and/or inhibit N-type calcium channels. Test peptides can be assessed for such binding or inhibiting, either alone or linked to an active agent, particularly an active peptide, sometimes known as a cargo peptide. Other internalization peptides that can be tested include antennapedia internalization peptide (Bonfanti, Cancer Res. 57, 1442-6 (1997)) (and variants thereof), Tat variants, Penetratin, SynB1 and 3, Transportan, Amphipathic, gp41NLS, polyArg, and others described in the following references (Temsamani, Drug Discovery Today, 9(23):1012-1019, 2004; De Coupade, Biochem J., 390:407-418, 2005; Saalik Bioconjugate Chem. 15: 1246-1253, 2004; Zhao, Medicinal Research Reviews 24(1): 1-12, 2004; Deshayes, Cellular and Molecular Life Sciences 62:1839-49, 2005) (all incorporated by reference).

X. Linkage of Tat Variants to Other Active Agents

The tat variants described above can be linked to any other active agent to promote uptake of the agent through cell membranes and/or the blood brain barrier. Use of a chimeric agent comprising or consisting of a tat variant and active agent in a therapeutic method improves bioavailability at the intended site relative to use of the active agent alone, and reduces side effects through binding to N-type calcium channels relative to use of the active agent linked to a standard tat peptide. The tat variants are particularly useful for active agents with an intracellular target and/or neuroactive drugs that need to cross the blood brain barrier to exert activity. Some but not all of the active agents amenable to attachment of tat variants are peptides. Use of tat variants is particularly useful for existing pharmaceuticals that have poor bioavailabilty, high dosages or short half-lives.

Some guidance for selection of active agents, methods for attachments and use thereof is provided by the scientific and patent literature relating to previous tat peptides (see, e.g., U.S. Pat. No. 6,316,003 and U.S. Pat. No. 5,804,604). All of the above description in relating to chimeric peptides comprising an active peptide linked to a tat variant for treatment of stroke and related diseases applies mutatis mutandis to chimeric agents comprising a tat variant linked to an active agent.

The table below lists the names of active agents (some of which are approved drugs), the disorders they are useful for treating, whether the disease is acute or chronic, the routes of administration of drugs (to the extent established) and comments on problems with existing drugs that may in part be overcome by the improved transport through membranes conferred by a tat variant peptide.

Chimeric agents comprising a tat variant peptide linked to an active agent can be used at the same or lower dosage on a molar basis as the active agent alone, and can be administered by the same route as the active agent alone, and for treatment of the same disease(s) as the active agent alone. The preferred methods of administration for peptide:active conjugates disclosures within are intravenous, intraarterial, intranasal/inhalation, intramusular, intraperitoneal, sub-lingual, per-rectum, and topical (for disorders of the dermis or proximal to epithelial cells).

TABLE 5

| Active Agent | Disease | Acute/chron | Route of admin | Comment | Reference |
| --- | --- | --- | --- | --- | --- |
| Phenobarbitol (luminal sodium) | Epilepsy | | IV/oral | Dependence, tolerance issues, interactions, side effects, birth defects | Motamedi & Meador (2006) Curr Neurol Neurosci Rep, 6(4): 341-6. Drugs.com |
| Myidone ®, Mysoline ® (primidone) | Epilepsy | | Oral | Side effects, interactions | Koristkova, et al (2006) Int J Clin Pharmacol Ther, 44(9): 438-42. Drugs.com |
| Valium ® (diazepam) | Anxiety | | IP/oral | Dependence, side effects, interactions | Beard, et al (2003) Health Technol Assess, 7(40): iii, ix-x, 1-111. Drugs.com |

TABLE 5-continued

| Active Agent | Disease | Acute/chron | Route of admin | Comment | Reference |
|---|---|---|---|---|---|
| Dopamine | Parkinson's | | | Cannot cross BBB, side effects | Ahlskog (2001) Neurol Clin, 19(3): 579-605. Drugs.com |
| Levodopa | Parkinson's | | | Degraded before BBB, side effects, halflife = 1.5 hrs | Nyholm (2006) Clin Pharmacokinet, 45(2): 109-36. USPTO.gov (patent # 7160913) |
| Apomorphine | | | IP | Short half-life | Nyholm (2006) Clin Pharmacokinet, 45(2): 109-36. Drugs.com |
| Freedox ® (tirilazad mesylate) | Stroke | | IP | Low efficacy, phase III stopped | Hickenbottom & Grotta (1998) Semin Neurol 18(4): 485-92. Strokecenter.org |
| Gengraf ® (cyclosporin) | Immune suppression | | IP | Peptide, 5-18 hr halflife | Kees, et al (2006) Ther Drug Monit, 28(3): 312-20. Drugs.com |
| Vacomycin | Antibiotic | | IP | Peptide, low uptake, 4-6 hr halflife | de Hoog, et al (2004) Clin Pharmacokinet, 43(7): 417-40. Drugs.com |
| Prinivil ® (lininopril) | Hypertension | | IP/oral | Peptide, poor BBB crossing, 12 hr halflife | Tan, et al (2005) Am J Hypertens, 18(2): 158-64. Drugs.com |
| Azidothymidine (AZT, Zidoridine ®, Combivir ®) | Antiviral | | Oral | Poor BBB crossing, 05-3 hr halflife, hematologic toxicology | Spitzenberger, et al (2006) J Cereb Blood Flow Metab, Oct 25, Epub ahead of print. Drugs.com |
| Piracetam | Pain/epilepsy | | | Cannot cross BBB | Loscher & Potschka (2002) J Pharmacol Exp Ther, 301(1): 7-14. U.S. Pat. No. 7,157,421) |
| Natrecor ® (nesiritide) (BNP peptide) | Cardio-renal decompensation syndrome | | IV | Unknown efficacy | Feldman & Sun (2004) Heart Fail Rev, 9(3): 203-8. Clinicaltrials.gov |
| AVR-118 (peptide) | Cancer palliative | | Subcutaneous | Unknown efficacy, unknown dosage | Clinicaltrials.gov |
| Oxytocin (peptide) | Mood disorders | | IV/IM | Interactions, unknown dosage | Swaab, et al (2005) Ageing Res Rev, 4(2): 141-94. Drugs.com |
| Pravachol ® (pravastatin) | MS | | Oral | Unknown efficacy, low bioavailability | Hatanaka (2000) Clin Pharmacokinet, 39(6): 397-412. Clinicaltrials.gov |
| Remifentanil | Pain, burn | | IV | 3.5 min halflife, metabolized by unknown esterase | Scott & Perry (2005) Drugs, 65(13): 1793-1823. Clinicaltrials.gov |

TABLE 5-continued

| Active Agent | Disease | Acute/chron | Route of admin | Comment | Reference |
|---|---|---|---|---|---|
| Neurotensin | Schizphrenia, parkinson's, addiction | | | 13AA peptide, easily degraded, cannot cross BBB | Boules, et al, (2006) Peptides, 27(10): 2523-33. |
| GDNF (glial derived neurotrophic factor) | Parkinson's | Chronic | Intra-parenchymal | Peptide, Cannot cross BBB | Grondin, et al (2003) Prog Drug Res, 61: 101-23. |
| Lopinavir Ritonavir Saquinavir Darunavir Atazanavir Amprenavir (protease inhibitors) | HIV | | Oral | All HIV protease inhibitors suffer from the acute capacity of HIV to mutate, generating drug resistant HIV strains | Oldfield & Plosker (2006) Drugs 66(9): 1275-99. Porter & Charman (2001) Adv Drug Deliv Rev, Oct 1; 50 Suppl 1: S127-47. Piacenti (2006) Pharmacotherapy 26(8): 1111-33. |
| Dihydroergotamine | Migraine | | IV, IM, sub-Q | Interactions cause peripheral ischemia, 9 hr halflife | Modi & Lowder (2006) Am Fam Physician 73(1): 72-8. |
| Sporamox ® (itaconazole) | Antifungal | | Oral | Drug resistance eventually develops, congestive heart failure in some populations | Wang & Remold (2006) Cardiol Rev 14(5): 223-6. |
| Protein Kinase C inhibitors | Acute myocardial infarction, stroke, ischemia, reperfusion injury | | | | US pat publications 20050267030, 20060148702, 20060293237, 20050215483, 20040204364, 20040009922 |
| AII-7 | Cancer, breast cancer | Chronic | | Peptidomimetic that blocks Erbb2 intracellular domain and increases taxol sensitivity | Kunz et al, Mol Cancer Res 2006; 4(12): 983-98 |
| CRAMP peptide | *Salmonella* infection | | | Intracellular anti-microbial peptide that reduces *Salmonella* replication | Rosenberger, CM. PNAS\| Feb. 24, 2004\|vol. 101\| no. 8\|2422-2427 |
| Sodium channel peptide | May reduce muscle spasms (epilepsy, restless leg, parkinsons, etc) | | | Peptide corresponding to the short intracellular segment between homologous transmembrane domains III and IV of sodium channel alpha subunit slowed inactivation | Vassilev, Science (1988) 241: 1658-6 |
| Aptamer KDI1 | Blocks EGF signaling - | | | | Buerger. J. Biol. Chem., |

TABLE 5-continued

| Active Agent | Disease | Acute/chron | Route of admin | Comment | Reference |
|---|---|---|---|---|---|
| | possible anti cancer | | | | Vol. 278, Issue 39, 37610-37621, Sep. 26, 2003 |
| RNA/gene therapy | | | | Transporter peptides can be used to bring in RNAs or siRNA/RNAi for treatment | Turner et al (2007) Blood Cells Mol Dis, 38(1): 1-7. |

Example 1

Screening for Side Effects of Tat-NR2B9c

Tat-NR2B9c is a chimeric peptide of a standard tat peptide and KLSSIESDV (SEQ ID NO:12) previously shown to be effective in a rat model of stroke. This example screens the peptide Tat-NR2B9c for capacity to inhibit binding of known ligands to about 70 receptors proteins. Examples of receptors screened included glutamate, histamine H1, potassium channels, Dopamine D1, calcium channels (L-type, N-type).

Tat-NR2B9c was found to inhibit binding to two such receptors, an N-type calcium channel and a chemokine CXCR2 (IL-8Rb). The screen was performed as a competitive binding assay in which unlabelled Tat-NR2B9c at a concentration of 10 µM competed with an I125 labeled ligand for binding to its receptor in the presence of unlabeled ligand to increase sensitivity. At 10 µM, Tat-NR2B9c showed 100% inhibition of radiolabeled ω-Conotoxin GVIA binding to N-type Ca channels. Tat-NR2B9c also showed 80% inhibition of IL-8/IL-8RB at the same concentration. Results are shown in FIGS. 1A, B, C.

Example 2

Mutagenesis of a Standard Tat Peptide

Like the known N-type calcium channel inhibiter Ziconotide, Tat-NR2B9c contains numerous positive charges. The positive charges presumably facilitate both the ability to cross the blood brain barrier and may also contribute to N-type calcium channel binding. Direct sequence comparison shows some similarity in positive (R=Arginine, K=Lysine) charges as well as spacing of these charges along the peptide backbone (see alignment below). This approximately maps the Tat-NR2B9c N-type calcium channel binding epitope to the Tat region (shown in italics) and one amino acid of the NMDAR2B domain.

```
YGRKKRRQRRRKLSSIESDV    (SEQ ID NO: 17)
                        (Tat-NR2B9c)

CKGKGAKCSRLMYDCCTGSCRSGKCG    (SEQ ID NO: 72)
                              (Ziconotide)
```

The present inventors hypothesized that mutation of the Y residue at position 1 of Tat-NR2B9c to F might reduce binding to N-type calcium channels without impairing cellular uptake of the drug. The inventors also hypothesized that modifications of a stretch of basic residues in the standard tat peptide would achieve a similar result. The peptides were each applied at 100 µM. The following peptides were tested (the $Ca^{2+}$ current in shown as a percentage after each peptide): 1990 TAT: YGRKKRRQRRR (SEQ ID NO:1) (57+/−1.6% (n=5)); 1991 2B9c: KLSSIESDV (SEQ ID NO:12) (94+/−1.7% (n=5)); 1992 Tat-NR2B9c-AA; YGRKKRRQR-RRKLSSIEADA (SEQ ID NO:18) (74+/−2.4% (n=6)); 1993 F-Tat-NR2B9c: FGRKKRRQRRRKLSSIESDV (SEQ ID NO:19) (91+/−1.6% (n=5)); 1994 Tat-NR2B9c K to A: YGRKKRRQRRRALSSIESDV (SEQ ID NO:20) (77+/−1.8% (n=7)); 1995 F-Tat-NR2B9c K to A: FGRKKRRQR-RRALSSIESDV (SEQ ID NO:21) (97+/−0.2% (n=6)); 1976: YGRKKRRQRRRKLSSIESDX (SEQ ID NO:22) where X=norvaline (66+/−3.4% (n=6)); 1977: YGRKKRRQR-RRKLSSIESDX (SEQ ID NO:23) where X=L-t-butyl-glycine (65+/−5.1% (n=5)); 1987: D-isomer of Tat-NR2B9c (82+/−2.2% (n=6)). Tat-NR2B9c (68+/−1.7% (n=7)). Data were plotted as mean+/−s.e.m.

The peptides were also tested in the following patch clamp assay. Internalization peptides and chimeric peptides were screened for their capacity to inhibit ionic currents mediated by N-type calcium channels. This was carried out by performing whole-cell patch clamp recordings in dorsal root ganglion neurons, in which N-type calcium currents are expressed. Cultures of dorsal root ganglions (DRGs) were prepared from Swiss mice at 13-14 d of gestation. In brief, DRG's were dissected and subjected to trypsin digestion for 20 min at 37° C., mechanically dissociated and plated on cover slips coated with poly-D-lysine. They were grown in serum free MEM (Neurobasal MEM, B-27-Gibco Invitrogen Corporation, Carlsbad, Calif.). After 3-5 days, 10 µM FUDR solution was added to inhibit glial proliferation. The cultures were maintained at 37° C. in a humidified 5% $CO_2$ atmosphere and were fed twice a week. Whole-cell recording were carried out at room temperature 10-14 days after plating. Electrophysiology recordings: Whole-cell recordings were performed with an Axopatch-1B amplifier (Axon Instruments, Foster City, Calif.) in the voltage-clamp mode. Recording electrodes, with resistances of 3-5 MΩ, were constructed from thin-walled borosilicate glass (1.5 mm diameter; World Precision Instruments, Sarasota, Fla.) using a two-stage puller (PP83; Narishige, Tokyo, Japan). Data were digitized, filtered (2 kHz), and acquired on-line using the programs of pClamp 9 (Axon Instruments). The pipettes were filled with a solution containing (mM): CsCl 110, MgCl2 3, EGTA 10, HEPES 10, MgATP 3, GTP 0.6. The pH was adjusted to 7.2 with CsOH. The bath solution contained (mM): CaCl2 1, BaCl2 10, HEPES 10, TEA-Cl 160, Glucose 10, TTX 0.0002 at pH (NaOH) 7.4. Whole-cell currents were elicited using 40 ms depolarizing pulses to +20 mV from a holding potential of −60 mV, applied every 15 s. To test the use-dependent inhibition, currents were elicited using 10 ms depolarizing pulses to +20 mV from a holding potential of −60 mV, applied every 0.02 s (50 Hz), 0.05 s (20 Hz), 0.1 s (10 Hz) or 15 s (0.07 Hz) respectively.

Results: The results are presented in FIG. 2. The upper portion represents the means+/−s.e.m. of whole cell calcium current in the presence of the indicated peptide normalized to the whole cell calcium current in the same cells before application of the peptide. The lower portion of FIG. 2 shows representative whole-cell traces from which the means in the upper portion were derived. In brief, the data show that the TAT transporter portion of the chimeric peptide is predominantly responsible for the inhibition of N-type calcium channels. Mutation of the N-terminal tyrosine of Tat-NR2B9c almost completely abrogates the ability of this chimeric peptide to inhibit N-type calcium channels. The C-terminal portion of Tat-NR2B9c (KLSSIESDV (SEQ ID NO:12)), F-Tat-NR2B9c or 1994 Tat-NR2B9c K to A showed no significant inhibition of N-type calcium channel activity. Peptides 1992, 1994 and 1987 showed significant improvement in channel activity over TAT alone although still displayed some reduction in the amount of N-type calcium channel activity. All of these peptides provide reduced binding to N-type calcium channels over standard Tat alone that indicate an increased therapeutic index of a drug that includes one of these Tat variant sequence.

Example 3

Further Analysis of Inhibition of N-Type $Ca^{2+}$ Channel-Mediated Ionic Currents by Tat-NR2B9c Further experiments were carried out as depicted in FIGS. 4-7. Their purpose was to further characterize the inhibition of N-type $Ca^{2+}$ channel-mediated ionic currents by Tat-NR2B9c. Additionally, FIG. 4 characterizes the degree of inhibition of the $Ca^{2+}$ current by Tat-NR2B9c (YGRKKRRQRRRKLSSIESDV, SEQ ID 17) and this is compared with the other variants: 1990 TAT (YGRKKRRQRRR, SEQ ID NO:1); 1992 Tat-NR2B9c AA (YGRKKRRQRRRKLSSIEADA, SEQ ID 18); 1994 Tat-NR2B9c KtoA (YGRKKRRQRRRALSSIESDV, SEQ ID 20); 1987 D-Tat-NR2B9c (YGRKKRRQRRRALSSIESDV (all D-amino acids), SEQ ID); 1976 (YGRKKRRQRRRKLSSIESDX, where X=norvaline, SEQ ID NO:22); 1977 (YGRKKRRQRRRKLSSIESDX, where X=L-t-butyl Glycine, SEQ ID NO:23).

Tissue Culture:

Cultures of dorsal root ganglions (DRGs) were prepared from Swiss mice at 13-14 d of gestation. Briefly, DRG's were dissected and subjected to trypsin digestion for 20 min at 37° C., mechanically dissociated and plated on cover slips coated with poly-D-lysine. They were grown in serum free MEM (Neurobasal MEM, B-27-Gibco Invitrogen Corporation, Carlsbad, Calif.). After 3-5 days, 10 μM FUDR solution was added to inhibit glial proliferation. The cultures were maintained at 37° C. in a humidified 5% $CO_2$ atmosphere and were fed twice a week. Whole-cell recording were carried out at room temperature 10-14 days after plating.

Electrophysiology Recordings:

Whole-cell recordings were performed with an Axopatch-1B amplifier (Axon Instruments, Foster City, Calif.) in the voltage-clamp mode. Recording electrodes, with resistances of 3-5 MΩ, were constructed from thin-walled borosilicate glass (1.5 mm diameter; World Precision Instruments, Sarasota, Fla.) using a two-stage puller (PP83; Narishige, Tokyo, Japan). Data were digitized, filtered (2 kHz), and acquired on-line using the programs of pClamp 9 (Axon Instruments).

The pipettes were filled with a solution containing (mM): CsCl 110, MgCl2 3, EGTA 10, HEPES 10, MgATP 3, GTP 0.6. The pH was adjusted to 7.2 with CsOH. The bath solution contained (mM): CaCl2 1, BaCl2 10, HEPES 10, TEA-Cl 160, Glucose 10, TTX 0.0002 at pH (NaOH) 7.4. Whole-cell currents were elicited using 40 ms depolarizing pulses to +20 mV from a holding potential of −60 mV, applied every 15 s. To test the use-dependent inhibition, currents were elicited using 10 ms depolarizing pulses to +20 mV from a holding potential of −60 mV, applied every 0.02 s (50 Hz), 0.05 s (20 Hz), 0.1 s (10 Hz) or 15 s (0.07 Hz) respectively.

Data Analysis:

Data were plotted as mean+/−s.e.m.

Figure 4:
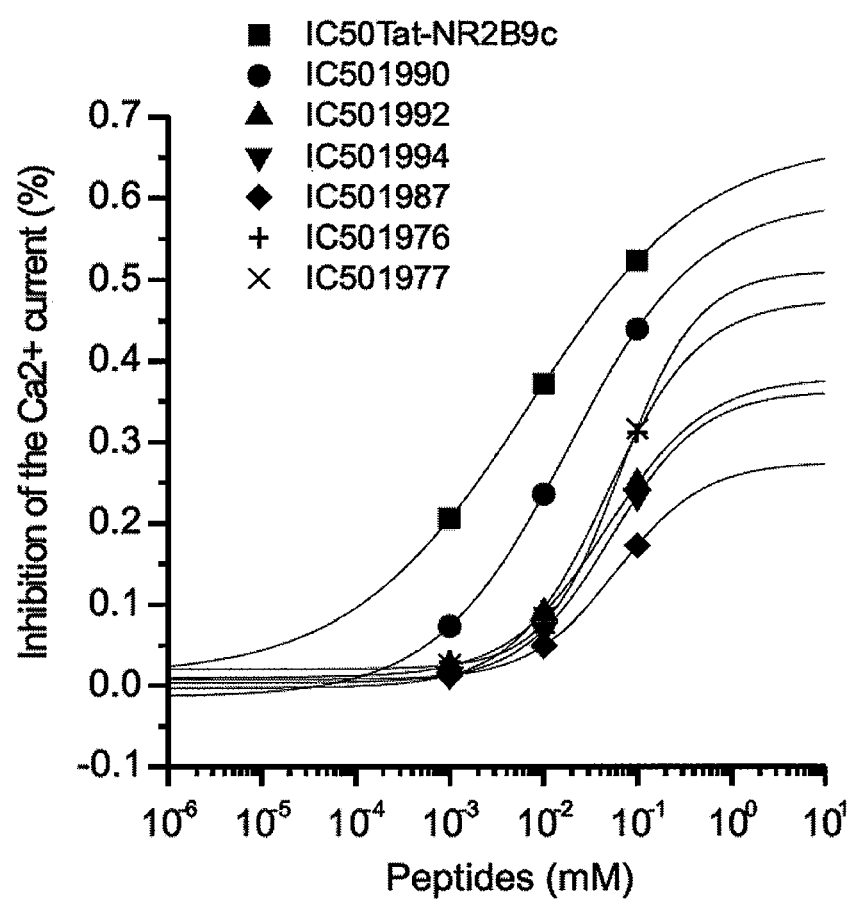
FIG. 4: $IC_{50}$ determination for certain of the peptides for N-type calcium currents in DRG neurons.

FIG. 4 demonstrates that increasing concentrations of all peptides containing an intact Tat sequence (YGRKKRRQRRR (SEQ ID NO:1)) significantly inhibit $Ca^{2+}$ currents in dorsal root ganglion neurons (which express predominantly N-type $Ca^{2+}$ channels). This suggests that the property of inhibiting N-type $Ca^{2+}$ channel currents resides in the Tat sequence.

Figure 5A:
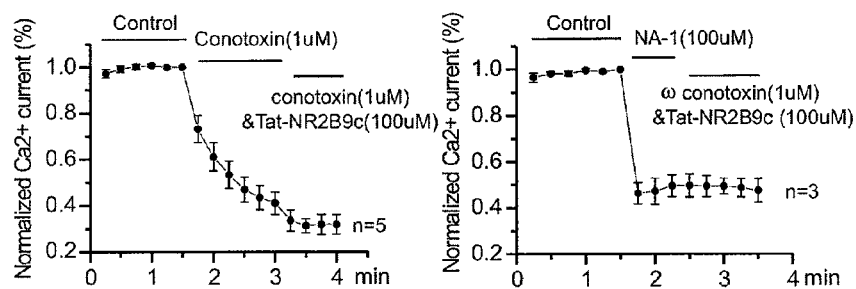
FIGS. 5A and 5B: Selectivity of Tat-NR2B9c for N-type calcium currents over L-type currents in DRG neurons.
Figure 5B:
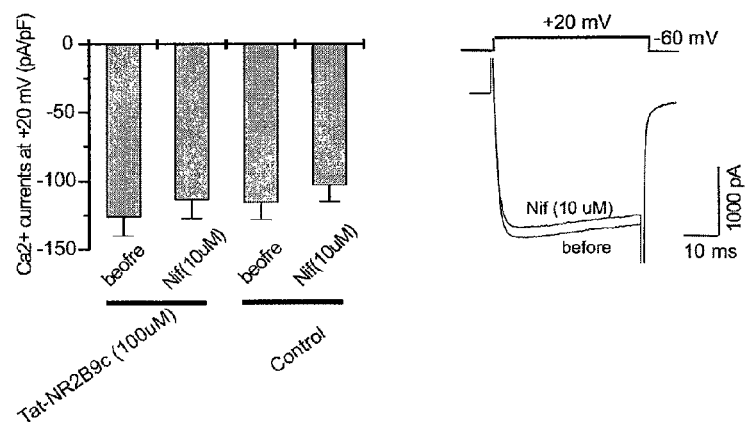

FIGS. 5A and B demonstrate that the inhibition of the $Ca^{2+}$ current by Tat-NR2B9c is specific to N-type $Ca^{2+}$ channels. Omega conotoxin (1 μM), a selective N-type $Ca^{2+}$ channel blocker, inhibits the $Ca^{2+}$ current, and no additional inhibition is afforded by Tat-NR2B9c (100 μM) once N-channels are blocked (FIG. 5A, left). Similarly, no additional inhibition of the current is seen when conotoxin is added after the inhibition of the ionic current by Tat-NR2B9c (FIG. 5A, right). Also, the selective L-type $Ca^{2+}$ channel blocker, nifedipine, does significantly affect the size of the $Ca^{2+}$ current recorded in the presence (100 μM intracellular), or absence of, Tat-NR2B9c as shown in FIG. 5B. The left portion of FIG. 5B shows the means+/−s.e.m.s of calcium currents, whereas on the right are representative traces of whole cell currents from a single experiment.

Figure 6:
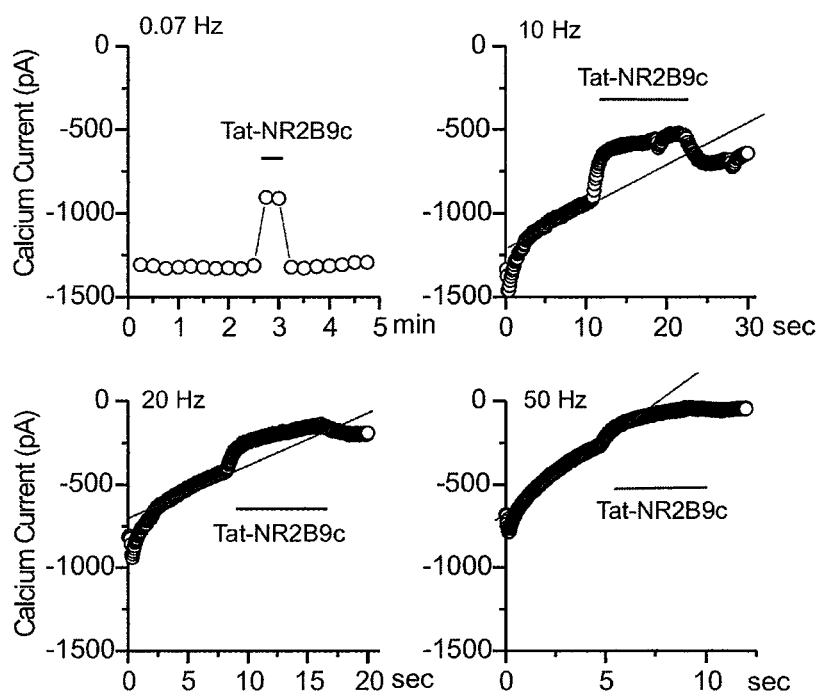
FIG. 6: Lack of use-dependence on N-type calcium current inhibition by Tat-NR2B9c. Currents were recorded in one representative DRG neuron by different frequency (0.07, 10, 20, 50 Hz). Tat-NR2B9c (100 µM) was applied as indicated. The currents shown strong frequency-dependent rundown, and the increase of frequency did not increase Tat-NR2B9c's inhibition effect.

FIG. 6 demonstrates that the block of $Ca^{2+}$ currents by Tat-NR2B9c is not frequency dependent. 100 μM Tat-NR2B9c was used to test its use-dependent effect. The currents elicited by depolarizing pulses of +20 mV showed strong frequency-dependent rundown. However, the increase of frequency (0.07, 10, 20, 50 Hz) did not increase Tat-NR2B9c's inhibition effect on this current. The figure shows $Ca^{2+}$ currents recorded in one representative DRG neuron at different frequencies. These currents have a natural tendency to run-down after a few minutes, and the increase in frequency had no effect on the inhibition of the current by Tat-NR2B9c (representative of n=4).

Figure 7:
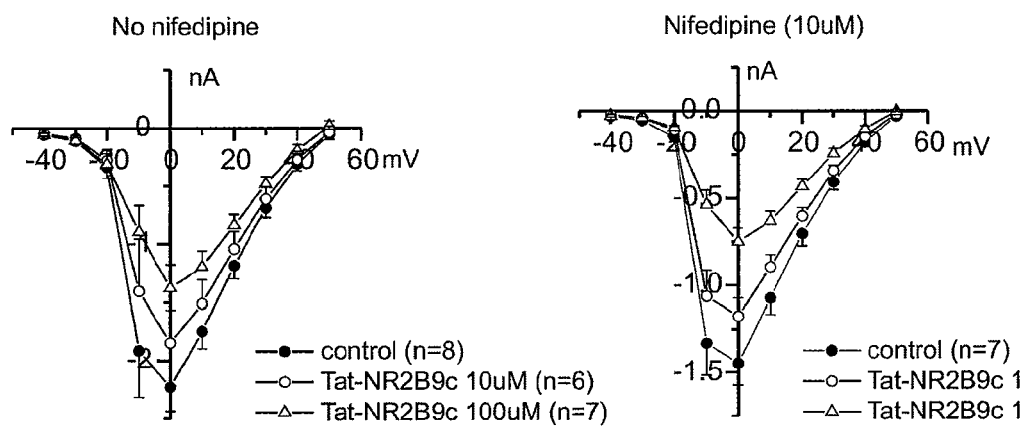
FIG. 7: Lack of voltage-dependent inhibition by Tat-NR2B9c of N-type calcium currents. The I-V relationships of $Ca^{2+}$ current in cultured DRG neurons. Tat-NR2B9c (10µ, 100 µM) was applied in the presence or absence of 10 µM nifedipine. The currents were elicited using 50 ms voltage-clamp steps from −40 to +50 mV from the holding potential of −60 mV.

FIG. 7 demonstrates that Tat-NR2B9c inhibits the $Ca^{2+}$ current in DRG neurons in a manner that is independent of voltage, and that this inhibition is specific to N-type $Ca^{2+}$ channels because it is not affected by nifedipine, a blocker of L-type $Ca^{2+}$ channels. The currents were elicited using 50 ms voltage-clamp steps from −40 to +50 mV from the holding potential of −60 mV.

In conclusion, FIGS. 4-7 show that the inhibition of $Ca^{2+}$ currents by Tat-NR2B92 is specific to N-type $Ca^{2+}$ channels, and is similarly a property of other peptides bearing the Tat moiety. The data also show that this inhibition is specific to N-type $Ca^{2+}$ channels, and is independent of frequency and of voltage.

Example 3

F-Tat-NR2B9c is Equally Effective in a Stroke Model

Figure 3A:
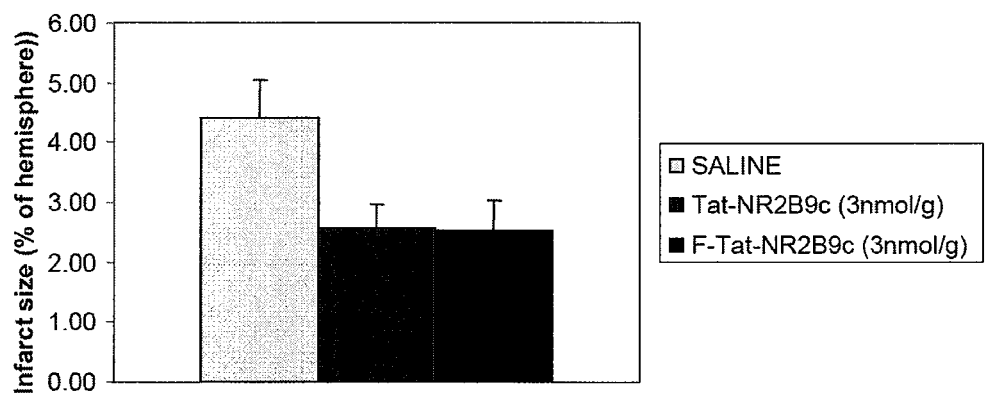
FIGS. 3A and 3B show (A) Effect of Tat-NR2B9c and F-Tat-NR2B9c on cerebral infarction volume in rats treated 1 h after onset of permanent ischemia using the pial vessel occlusion model (10 rats/group); and (B) Serial brain sections of a representative rat from each group stained with triphenyl-tetrazolium chloride (TTC).
Figure 3B:
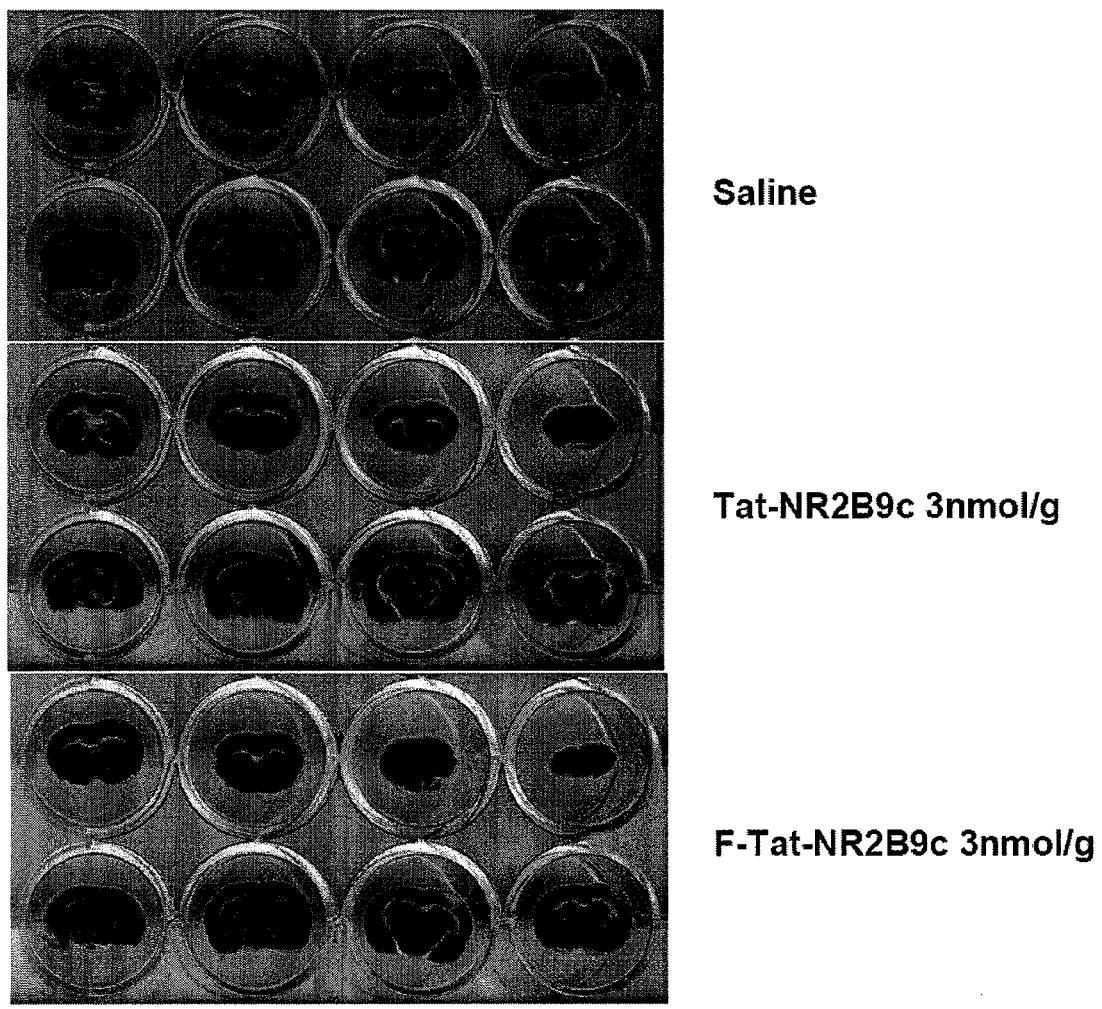

F-Tat-NR2B9c was compared with Tat-NR2B9c at a single does of 3 nmol/g weight in the rat pial occlusion model of permanent ischemia described above and further in example 4. In both cases, the chimeric peptide was administered one hour after initiating ischemia. F-Tat-NR2B9c and Tat-NR2B9c were equally effective in reducing infarct size as shown in FIG. 3.

Example 4

Purpose:
1. To test the neuroprotective efficacy of the Tat-NR2B9c peptide in both male and female rats using the in vivo pial 3 vessel occlusion (P3VO) model of stroke.
2. To elucidate the mechanism of action by testing 6 variations of the Tat-NR2B9c peptide in male rats.

Background:

The peptide known as Tat-NR2B9c has been developed and previously tested in the MCAO model of stroke in the rat. This peptide has been shown to be neuroprotective as seen by a reduced infarct size. However, the MCAO model of stroke results in a large infarct with extensive neurological deficits and shortened life span. The P3VO model of stroke results in a much smaller, cortical infarct with minimal neurological deficit and normal life span.

Six additional peptides were tested that contain the same amino acid sequence as Tat-NR2B9c except for the terminal 3 amino acids. By varying these amino acids and then testing the neuroprotective efficacy of the peptides in the P3VO model of stroke, the mechanism of action can be further elucidated.

The amino acid structure of Tat-NR2B9c and the 6 peptides are as follows:

```
Sequence:           Name:

YGRKKRRQRRRKLSSIESDVTat-NR2B9c
                    (SEQ ID NO: 17)

YGRKKRRQRRRKLSSIESDXX = 3-fluoro-DL-Valine 1974
                    (SEQ ID NO: 73)

YGRKKRRQRRRKLSSIETDXX = norvaline 1975
                    (SEQ ID NO: 74)

YGRKKRRQRRRKLSSIESDXX = norvaline 1976
                    (SEQ ID NO: 22)

YGRKKRRQRRRKLSSIESDXX = L-t-butyl-glycine 1977
                    (SEQ ID NO: 23)

YGRKKRRQRRRKLSSIEXDVX = L-2-amino-3-
                        ureidopropionic acid 1978
                    (SEQ ID NO: 75)

YGRKKRRQRRRKLSSIETAL1980
                    (SEQ ID NO: 76)
```

Methods:

Animals

Adult Sprague Dawley rats (10-12 weeks old) (males ~300 g, females ~250 g) (FIG. 8) were fasted for 12-18 hours before being subjected to permanent pial vessel occlusion of 3 terminal branches of the Middle Cerebral Artery over the Whisker Barrel Cortex (P3VO). Each of 7 peptides were tested in male rats plus a saline control group (n=8 in each group). The Tat-NR2B9c peptide and a saline control group were tested in female rats (n=8 in each group). The researcher was blinded to the treatment group during the time of surgery through to the analysis of infarct size.

General Procedure

Rats were anesthetized with a 0.5 ml/kg intramuscular injection of ketamine (100 mg/kg), acepromazine (2 mg/kg), and xylazine (5 mg/kg), supplemented with one third the initial dose as required. An anal temperature probe was inserted and the animal was placed on a heating pad maintained at 37° C. The right external carotid artery (ECA) was cannulated with PE 10 polyethylene tubing for dye injections. The skull was exposed via a midline incision, scraped free of tissue, and the temporalis muscle disconnected from the skull on the right side. Using a dissecting microscope and a pneumatic dental drill, a 6×4 mm cranial window was made over the right somatosensory cortex (2 mm caudal and 5 mm lateral to bregma) by drilling a rectangle through the skull and lifting off the piece of skull while keeping the dura intact. After being bathed with artificial cerebrospinal fluid, small boluses (10 to 20 μL) of the vital dye patent blue violet (10 mmol/L; Sigma) in normal saline, were injected into the right external carotid artery to demonstrate transit through surface vessels of the cortex. Three critical arteriolar branches of the MCA around the barrel cortex were selected and electrically cauterized through the dura. After the cauterizations, the bolus injections and dye transits were repeated to ensure transits through the cauterized arterioles were blocked. The rectangle of skull was replaced over the window and the scalp was sutured. The catheter was removed from the ECA, the ECA was ligated, and the anterior neck was sutured. One hour after initiation of focal occlusion, 0.3 ml of drug (3 nMol/g body weight) or saline control were infused through the tail vein at a rate of 0.06 ml/min. Each rat was returned to its individual cage under a heating lamp to maintain body temperature until the rat fully recovered. Food and water was supplied ad libitum.

Harvesting of Brain Tissue

Twenty-four hours post-surgery, animals were re-anesthetized with 1 mL pentobarbital and the brain was quickly harvested. One coronal slice was taken through the infarct region and incubated in 2% triphenyltetrazolium chloride (TTC) for 15 minutes at 37° C. Images were scanned and brain slices were stored at −80° C.

Analysis

Infarct size was measured as a percent of the hemisphere for each rat in the study. After obtaining infarct size measurements, the animals were separated into their respective groups. Comparisons were made between treatment groups as means±SE.

Figure 8:
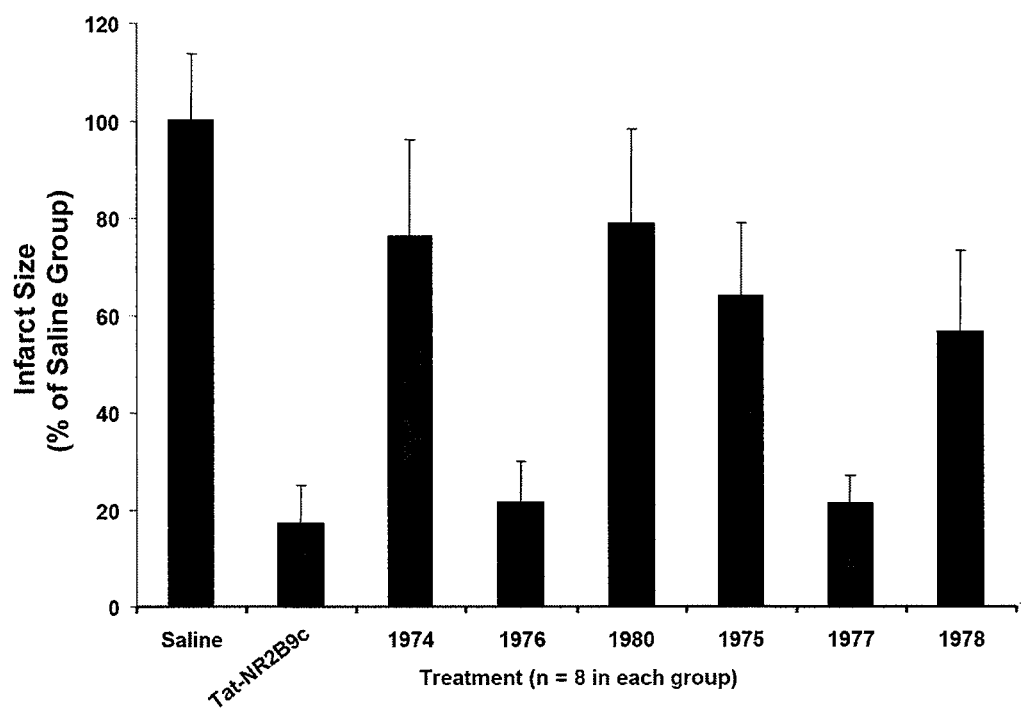
FIG. 8: Assessment of neuroprotection observed using alternative C-terminal sequences in the pial occlusion model of permanent ischemia in rats.

Results:

Of the six novel peptides tested, Tat-NR2B9c, 1976 and 1977 resulted in a significantly decreased infarct sizes and 1975 and 1978 displayed some reduction in infarct size (FIG. 8).

All publications, and patent filings cited in this specification are herein incorporated by reference as if each individual publication or patent were specifically and individually indicated to be incorporated by reference. Genbank records referenced by Genbank identification (GID) or accession number, particularly any polypeptide sequence, polynucleotide sequences or annotation thereof, are incorporated by reference herein. If more than one version of a sequence has been associated with the same accession number at different times, reference to a deposit number should be construed as applying to the version in existence at the effective filing date of the application dating back to a priority application if the deposit is also referenced in the priority application. Various changes may be made and equivalents may be substituted without departing from the true spirit and scope of the invention. Unless otherwise apparent from the context, any feature, step or embodiment can be used in combination with any other feature, step or embodiment.

What is claimed is:

1. An isolated chimeric agent, wherein the chimeric agent comprises an active agent and an internalization peptide that promotes uptake of the chimeric agent into cells, wherein the internalization peptide is a variant of the tat peptide YGRKKRRQRRR (SEQ ID NO:1) that has reduced capacity to bind to an N-type calcium channel relative to the tat peptide and the variant has an amino acid sequence comprising FGRKKRRQRRR (SEQ ID NO:135).

2. The isolated chimeric agent of claim 1, wherein the active agent is an active agent shown in Table 5.

3. The isolated chimeric agent of claim 1, wherein the chimeric agent has a kD greater than 10 nM for an N-type calcium channel.

4. A pharmaceutical composition comprising the isolated chimeric agent claim 1 and a pharmaceutically acceptable carrier.

5. An isolated internalization peptide having an amino acid sequence comprising FGRKKRRQRRR (SEQ ID NO:135).

6. The isolated internalization peptide of claim 5 wherein the internalization peptide has a Kd greater than 10 nM for an N-type calcium channel blocking agent.

7. In a chimeric agent comprising an internalization peptide linked to an active agent, the improvement wherein the internalization peptide has an amino acid sequence comprising FGRKKRRQRRR (SEQ ID NO:135).

* * * * *

SEQUENCE LISTING

<160> NUMBER OF SEQ ID NOS: 136

<210> SEQ ID NO 1
<211> LENGTH: 11
<212> TYPE: PRT
<213> ORGANISM: Artificial
<220> FEATURE:
<223> OTHER INFORMATION: Synthetic tat peptide

<400> SEQUENCE: 1

Tyr Gly Arg Lys Lys Arg Arg Gln Arg Arg Arg
1               5                   10

<210> SEQ ID NO 2
<211> LENGTH: 11
<212> TYPE: PRT
<213> ORGANISM: Artificial
<220> FEATURE:
<223> OTHER INFORMATION: Synthetic internalization peptide
<220> FEATURE:
<221> NAME/KEY: MOD_RES
<222> LOCATION: (1)..(1)
<223> OTHER INFORMATION: Xaa is any amino acid other than Tyr or absent

<400> SEQUENCE: 2

Xaa Gly Arg Lys Lys Arg Arg Gln Arg Arg Arg
1               5                   10

<210> SEQ ID NO 3
<211> LENGTH: 11
<212> TYPE: PRT
<213> ORGANISM: Artificial
<220> FEATURE:
<223> OTHER INFORMATION: Synthetic internalization peptide

<400> SEQUENCE: 3

Gly Arg Lys Lys Arg Arg Gln Arg Arg Arg Pro
1               5                   10

<210> SEQ ID NO 4
<211> LENGTH: 19
<212> TYPE: PRT
<213> ORGANISM: Artificial
<220> FEATURE:
<223> OTHER INFORMATION: Synthetic chimeric peptide

<400> SEQUENCE: 4

Gly Arg Lys Lys Arg Arg Gln Arg Arg Arg Lys Leu Ser Ser Ile Glu
1               5                   10                  15

Ser Asp Val

<210> SEQ ID NO 5
<211> LENGTH: 4
<212> TYPE: PRT
<213> ORGANISM: Artificial
<220> FEATURE:
<223> OTHER INFORMATION: Synthetic active peptide
<220> FEATURE:
<221> NAME/KEY: MOD_RES
<222> LOCATION: (1)..(1)
<223> OTHER INFORMATION: Xaa = Glu, Asp, Asn or Gln
<220> FEATURE:
<221> NAME/KEY: MOD_RES
<222> LOCATION: (2)..(2)
<223> OTHER INFORMATION: Xaa = Ser or Thr
<220> FEATURE:
<221> NAME/KEY: MOD_RES
<222> LOCATION: (3)..(3)
<223> OTHER INFORMATION: Xaa = Asp, Glu, Gln or Asn

```
<220> FEATURE:
<221> NAME/KEY: MOD_RES
<222> LOCATION: (4)..(4)
<223> OTHER INFORMATION: Xaa = Val or Leu

<400> SEQUENCE: 5

Xaa Xaa Xaa Xaa
1

<210> SEQ ID NO 6
<211> LENGTH: 4
<212> TYPE: PRT
<213> ORGANISM: Artificial
<220> FEATURE:
<223> OTHER INFORMATION: Synthetic active peptide

<400> SEQUENCE: 6

Glu Ser Asp Val
1

<210> SEQ ID NO 7
<211> LENGTH: 4
<212> TYPE: PRT
<213> ORGANISM: Artificial
<220> FEATURE:
<223> OTHER INFORMATION: Synthetic active peptide

<400> SEQUENCE: 7

Glu Ser Glu Val
1

<210> SEQ ID NO 8
<211> LENGTH: 4
<212> TYPE: PRT
<213> ORGANISM: Artificial
<220> FEATURE:
<223> OTHER INFORMATION: Synthetic active peptide

<400> SEQUENCE: 8

Glu Thr Asp Val
1

<210> SEQ ID NO 9
<211> LENGTH: 4
<212> TYPE: PRT
<213> ORGANISM: Artificial
<220> FEATURE:
<223> OTHER INFORMATION: Synthetic active peptide

<400> SEQUENCE: 9

Glu Thr Glu Val
1

<210> SEQ ID NO 10
<211> LENGTH: 4
<212> TYPE: PRT
<213> ORGANISM: Artificial
<220> FEATURE:
<223> OTHER INFORMATION: Synthetic active peptide

<400> SEQUENCE: 10

Asp Thr Asp Val
1

<210> SEQ ID NO 11
<211> LENGTH: 4
<212> TYPE: PRT
```

```
<213> ORGANISM: Artificial
<220> FEATURE:
<223> OTHER INFORMATION: Synthetic active peptide

<400> SEQUENCE: 11

Asp Thr Glu Val
1

<210> SEQ ID NO 12
<211> LENGTH: 9
<212> TYPE: PRT
<213> ORGANISM: Artificial
<220> FEATURE:
<223> OTHER INFORMATION: Synthetic active peptide - 1991 2B9c

<400> SEQUENCE: 12

Lys Leu Ser Ser Ile Glu Ser Asp Val
1               5

<210> SEQ ID NO 13
<211> LENGTH: 9
<212> TYPE: PRT
<213> ORGANISM: Artificial
<220> FEATURE:
<223> OTHER INFORMATION: Synthetic active peptide

<400> SEQUENCE: 13

Lys Leu Ser Ser Ile Glu Thr Asp Val
1               5

<210> SEQ ID NO 14
<211> LENGTH: 3
<212> TYPE: PRT
<213> ORGANISM: Artificial
<220> FEATURE:
<223> OTHER INFORMATION: Synthetic active peptide
<220> FEATURE:
<221> NAME/KEY: MOD_RES
<222> LOCATION: (1)..(1)
<223> OTHER INFORMATION: Xaa is Thr or Ser
<220> FEATURE:
<221> NAME/KEY: MOD_RES
<222> LOCATION: (2)..(2)
<223> OTHER INFORMATION: Xaa is any amino acid
<220> FEATURE:
<221> NAME/KEY: MOD_RES
<222> LOCATION: (3)..(3)
<223> OTHER INFORMATION: Xaa is Val or Leu

<400> SEQUENCE: 14

Xaa Xaa Xaa
1

<210> SEQ ID NO 15
<211> LENGTH: 12
<212> TYPE: PRT
<213> ORGANISM: Artificial
<220> FEATURE:
<223> OTHER INFORMATION: Synthetic internalization peptide

<400> SEQUENCE: 15

Gly Arg Lys Lys Arg Arg Gln Arg Arg Arg Pro Gln
1               5                   10

<210> SEQ ID NO 16
<211> LENGTH: 20
<212> TYPE: PRT
<213> ORGANISM: Artificial
<220> FEATURE:
```

<223> OTHER INFORMATION: Synthetic chimeric peptide

<400> SEQUENCE: 16

Phe Gly Arg Lys Lys Arg Arg Gln Arg Arg Lys Leu Ser Ser Ile
1               5                   10                  15

Glu Thr Asp Val
            20

<210> SEQ ID NO 17
<211> LENGTH: 20
<212> TYPE: PRT
<213> ORGANISM: Artificial
<220> FEATURE:
<223> OTHER INFORMATION: Synthetic peptide

<400> SEQUENCE: 17

Tyr Gly Arg Lys Lys Arg Arg Gln Arg Arg Lys Leu Ser Ser Ile
1               5                   10                  15

Glu Ser Asp Val
            20

<210> SEQ ID NO 18
<211> LENGTH: 20
<212> TYPE: PRT
<213> ORGANISM: Artificial
<220> FEATURE:
<223> OTHER INFORMATION: Synthetic peptide - 1992 Tat-NR2B9c-AA

<400> SEQUENCE: 18

Tyr Gly Arg Lys Lys Arg Arg Gln Arg Arg Lys Leu Ser Ser Ile
1               5                   10                  15

Glu Ala Asp Ala
            20

<210> SEQ ID NO 19
<211> LENGTH: 20
<212> TYPE: PRT
<213> ORGANISM: Artificial
<220> FEATURE:
<223> OTHER INFORMATION: Synthetic peptide - 1993 F-Tat-NR2B9c

<400> SEQUENCE: 19

Phe Gly Arg Lys Lys Arg Arg Gln Arg Arg Lys Leu Ser Ser Ile
1               5                   10                  15

Glu Ser Asp Val
            20

<210> SEQ ID NO 20
<211> LENGTH: 20
<212> TYPE: PRT
<213> ORGANISM: Artificial
<220> FEATURE:
<223> OTHER INFORMATION: Synthetic peptide - 1994 Tat-NR2B9c K to A

<400> SEQUENCE: 20

Tyr Gly Arg Lys Lys Arg Arg Gln Arg Arg Ala Leu Ser Ser Ile
1               5                   10                  15

Glu Ser Asp Val
            20

<210> SEQ ID NO 21
<211> LENGTH: 20
<212> TYPE: PRT
<213> ORGANISM: Artificial

```
<220> FEATURE:
<223> OTHER INFORMATION: Synthetic peptide - 1995 F-Tat-NR2B9c K to A

<400> SEQUENCE: 21

Phe Gly Arg Lys Lys Arg Arg Gln Arg Arg Ala Leu Ser Ser Ile
1               5                   10                  15

Glu Ser Asp Val
            20

<210> SEQ ID NO 22
<211> LENGTH: 20
<212> TYPE: PRT
<213> ORGANISM: Artificial
<220> FEATURE:
<223> OTHER INFORMATION: Synthetic peptide variant- 1976
<220> FEATURE:
<221> NAME/KEY: MOD_RES
<222> LOCATION: (20)..(20)
<223> OTHER INFORMATION: Xaa is Nva

<400> SEQUENCE: 22

Tyr Gly Arg Lys Lys Arg Arg Gln Arg Arg Lys Leu Ser Ser Ile
1               5                   10                  15

Glu Ser Asp Xaa
            20

<210> SEQ ID NO 23
<211> LENGTH: 20
<212> TYPE: PRT
<213> ORGANISM: Artificial
<220> FEATURE:
<223> OTHER INFORMATION: Synthetic peptide - 1977
<220> FEATURE:
<221> NAME/KEY: MOD_RES
<222> LOCATION: (20)..(20)
<223> OTHER INFORMATION: Xaa is L-t-butyl-glycine

<400> SEQUENCE: 23

Tyr Gly Arg Lys Lys Arg Arg Gln Arg Arg Lys Leu Ser Ser Ile
1               5                   10                  15

Glu Ser Asp Xaa
            20

<210> SEQ ID NO 24
<211> LENGTH: 20
<212> TYPE: PRT
<213> ORGANISM: Artificial
<220> FEATURE:
<223> OTHER INFORMATION: Synthetic peptide

<400> SEQUENCE: 24

Phe Asn Gly Ser Ser Asn Gly His Val Tyr Glu Lys Leu Ser Ser Ile
1               5                   10                  15

Glu Ser Asp Val
            20

<210> SEQ ID NO 25
<211> LENGTH: 20
<212> TYPE: PRT
<213> ORGANISM: Artificial
<220> FEATURE:
<223> OTHER INFORMATION: Synthetic peptide - C-terminal 20mer sequence

<400> SEQUENCE: 25

His Pro Thr Asp Ile Thr Gly Pro Leu Asn Leu Ser Asp Pro Ser Val
1               5                   10                  15
```

```
Ser Thr Val Val
            20

<210> SEQ ID NO 26
<211> LENGTH: 20
<212> TYPE: PRT
<213> ORGANISM: Artificial
<220> FEATURE:
<223> OTHER INFORMATION: Synthetic peptide - C-terminal 20mer sequence

<400> SEQUENCE: 26

Arg Arg Ala Ile Glu Arg Glu Glu Gly Gln Leu Gln Leu Cys Ser Arg
1               5                   10                  15

His Arg Glu Ser
            20

<210> SEQ ID NO 27
<211> LENGTH: 20
<212> TYPE: PRT
<213> ORGANISM: Artificial
<220> FEATURE:
<223> OTHER INFORMATION: Synthetic peptide - C-terminal 20mer sequence

<400> SEQUENCE: 27

Thr Gln Gly Phe Pro Gly Pro Cys Thr Trp Arg Arg Ile Ser Ser Leu
1               5                   10                  15

Glu Ser Glu Val
            20

<210> SEQ ID NO 28
<211> LENGTH: 20
<212> TYPE: PRT
<213> ORGANISM: Artificial
<220> FEATURE:
<223> OTHER INFORMATION: Synthetic peptide - C-terminal 20mer sequence

<400> SEQUENCE: 28

Ala Val Ser Arg Lys Thr Glu Leu Glu Glu Tyr Gln Arg Thr Ser Arg
1               5                   10                  15

Thr Cys Glu Ser
            20

<210> SEQ ID NO 29
<211> LENGTH: 20
<212> TYPE: PRT
<213> ORGANISM: Artificial
<220> FEATURE:
<223> OTHER INFORMATION: Synthetic peptide - C-terminal 20mer sequence

<400> SEQUENCE: 29

Leu Asn Ser Cys Ser Asn Arg Arg Val Tyr Lys Lys Met Pro Ser Ile
1               5                   10                  15

Glu Ser Asp Val
            20

<210> SEQ ID NO 30
<211> LENGTH: 20
<212> TYPE: PRT
<213> ORGANISM: Artificial
<220> FEATURE:
<223> OTHER INFORMATION: Synthetic peptide - C-terminal 20mer sequence

<400> SEQUENCE: 30

Gly Gly Asp Leu Gly Thr Arg Arg Gly Ser Ala His Phe Ser Ser Leu
```

Glu Ser Glu Val
        20

<210> SEQ ID NO 31
<211> LENGTH: 20
<212> TYPE: PRT
<213> ORGANISM: Artificial
<220> FEATURE:
<223> OTHER INFORMATION: Synthetic peptide - C-terminal 20mer sequence

<400> SEQUENCE: 31

Gln Pro Thr Pro Thr Leu Gly Leu Asn Leu Gly Asn Asp Pro Asp Arg
1               5                   10                  15

Gly Thr Ser Ile
        20

<210> SEQ ID NO 32
<211> LENGTH: 20
<212> TYPE: PRT
<213> ORGANISM: Artificial
<220> FEATURE:
<223> OTHER INFORMATION: Synthetic peptide - C-terminal 20mer sequence

<400> SEQUENCE: 32

Met Gln Ser Ile Pro Cys Met Ser His Ser Ser Gly Met Pro Leu Gly
1               5                   10                  15

Ala Thr Gly Leu
        20

<210> SEQ ID NO 33
<211> LENGTH: 20
<212> TYPE: PRT
<213> ORGANISM: Artificial
<220> FEATURE:
<223> OTHER INFORMATION: Synthetic peptide - C-terminal 20mer sequence

<400> SEQUENCE: 33

Gln Asn Phe Ala Thr Tyr Lys Glu Gly Tyr Asn Val Tyr Gly Ile Glu
1               5                   10                  15

Ser Val Lys Ile
        20

<210> SEQ ID NO 34
<211> LENGTH: 20
<212> TYPE: PRT
<213> ORGANISM: Artificial
<220> FEATURE:
<223> OTHER INFORMATION: Synthetic peptide - C-terminal 20mer sequence

<400> SEQUENCE: 34

Gln Asn Tyr Ala Thr Tyr Arg Glu Gly Tyr Asn Val Tyr Gly Thr Glu
1               5                   10                  15

Ser Val Lys Ile
        20

<210> SEQ ID NO 35
<211> LENGTH: 20
<212> TYPE: PRT
<213> ORGANISM: Artificial
<220> FEATURE:
<223> OTHER INFORMATION: Synthetic peptide - C-terminal 20mer sequence

<400> SEQUENCE: 35

```
His Thr Gly Thr Ala Ile Arg Gln Ser Ser Gly Leu Ala Val Ile Ala
1               5                   10                  15

Ser Asp Leu Pro
            20

<210> SEQ ID NO 36
<211> LENGTH: 20
<212> TYPE: PRT
<213> ORGANISM: Artificial
<220> FEATURE:
<223> OTHER INFORMATION: Synthetic peptide - C-terminal 20mer sequence

<400> SEQUENCE: 36

Ser Phe Thr Ser Ile Leu Thr Cys His Gln Arg Arg Thr Gln Arg Lys
1               5                   10                  15

Glu Thr Val Ala
            20

<210> SEQ ID NO 37
<211> LENGTH: 20
<212> TYPE: PRT
<213> ORGANISM: Artificial
<220> FEATURE:
<223> OTHER INFORMATION: Synthetic peptide - C-terminal 20mer sequence

<400> SEQUENCE: 37

Glu Val Ile Asn Met His Thr Phe Asn Asp Arg Arg Leu Pro Gly Lys
1               5                   10                  15

Glu Thr Met Ala
            20

<210> SEQ ID NO 38
<211> LENGTH: 20
<212> TYPE: PRT
<213> ORGANISM: Artificial
<220> FEATURE:
<223> OTHER INFORMATION: Synthetic peptide - C-terminal 20mer sequence

<400> SEQUENCE: 38

Arg Arg Leu Pro Gly Lys Asp Ser Met Ala Cys Ser Thr Ser Leu Ala
1               5                   10                  15

Pro Val Phe Pro
            20

<210> SEQ ID NO 39
<211> LENGTH: 4
<212> TYPE: PRT
<213> ORGANISM: Artificial
<220> FEATURE:
<223> OTHER INFORMATION: Synthetic peptide - C-terminal 4mer sequence

<400> SEQUENCE: 39

Ser Thr Val Val
1

<210> SEQ ID NO 40
<211> LENGTH: 4
<212> TYPE: PRT
<213> ORGANISM: Artificial
<220> FEATURE:
<223> OTHER INFORMATION: Synthetic peptide - C-terminal 4mer sequence

<400> SEQUENCE: 40

His Arg Glu Ser
1
```

```
<210> SEQ ID NO 41
<211> LENGTH: 4
<212> TYPE: PRT
<213> ORGANISM: Artificial
<220> FEATURE:
<223> OTHER INFORMATION: Synthetic peptide - C-terminal 4mer sequence

<400> SEQUENCE: 41

Thr Cys Glu Ser
1

<210> SEQ ID NO 42
<211> LENGTH: 4
<212> TYPE: PRT
<213> ORGANISM: Artificial
<220> FEATURE:
<223> OTHER INFORMATION: Synthetic peptide - C-terminal 4mer sequence

<400> SEQUENCE: 42

Gly Thr Ser Ile
1

<210> SEQ ID NO 43
<211> LENGTH: 4
<212> TYPE: PRT
<213> ORGANISM: Artificial
<220> FEATURE:
<223> OTHER INFORMATION: Synthetic peptide - C-terminal 4mer sequence

<400> SEQUENCE: 43

Ala Thr Gly Leu
1

<210> SEQ ID NO 44
<211> LENGTH: 4
<212> TYPE: PRT
<213> ORGANISM: Artificial
<220> FEATURE:
<223> OTHER INFORMATION: Synthetic peptide - C-terminal 4mer sequence

<400> SEQUENCE: 44

Ser Val Lys Ile
1

<210> SEQ ID NO 45
<211> LENGTH: 4
<212> TYPE: PRT
<213> ORGANISM: Artificial
<220> FEATURE:
<223> OTHER INFORMATION: Synthetic peptide - C-terminal 4mer sequence

<400> SEQUENCE: 45

Ser Asp Leu Pro
1

<210> SEQ ID NO 46
<211> LENGTH: 4
<212> TYPE: PRT
<213> ORGANISM: Artificial
<220> FEATURE:
<223> OTHER INFORMATION: Synthetic peptide - C-terminal 4mer sequence

<400> SEQUENCE: 46

Glu Thr Val Ala
1
```

<210> SEQ ID NO 47
<211> LENGTH: 4
<212> TYPE: PRT
<213> ORGANISM: Artificial
<220> FEATURE:
<223> OTHER INFORMATION: Synthetic peptide - C-terminal 4mer sequence

<400> SEQUENCE: 47

Glu Thr Met Ala
1

<210> SEQ ID NO 48
<211> LENGTH: 4
<212> TYPE: PRT
<213> ORGANISM: Artificial
<220> FEATURE:
<223> OTHER INFORMATION: Synthetic peptide - C-terminal 4mer sequence

<400> SEQUENCE: 48

Pro Val Phe Pro
1

<210> SEQ ID NO 49
<211> LENGTH: 11
<212> TYPE: PRT
<213> ORGANISM: Artificial
<220> FEATURE:
<223> OTHER INFORMATION: Synthetic tat variant internalization peptide

<400> SEQUENCE: 49

Phe Gly Arg Lys Lys Arg Arg Gln Arg Arg Arg
1               5                   10

<210> SEQ ID NO 50
<211> LENGTH: 10
<212> TYPE: PRT
<213> ORGANISM: Artificial
<220> FEATURE:
<223> OTHER INFORMATION: Synthetic tat variant internalization peptide

<400> SEQUENCE: 50

Gly Arg Lys Lys Arg Arg Gln Arg Arg Arg
1               5                   10

<210> SEQ ID NO 51
<211> LENGTH: 5
<212> TYPE: PRT
<213> ORGANISM: Artificial
<220> FEATURE:
<223> OTHER INFORMATION: Synthetic peptide

<400> SEQUENCE: 51

Thr Gly Glu Lys Pro
1               5

<210> SEQ ID NO 52
<211> LENGTH: 8
<212> TYPE: PRT
<213> ORGANISM: Artificial
<220> FEATURE:
<223> OTHER INFORMATION: Synthetic peptide

<400> SEQUENCE: 52

Gly Gly Arg Arg Gly Gly Gly Ser
1               5

```
<210> SEQ ID NO 53
<211> LENGTH: 9
<212> TYPE: PRT
<213> ORGANISM: Artificial
<220> FEATURE:
<223> OTHER INFORMATION: Synthetic peptide

<400> SEQUENCE: 53

Leu Arg Gln Arg Asp Gly Glu Arg Pro
1               5

<210> SEQ ID NO 54
<211> LENGTH: 19
<212> TYPE: PRT
<213> ORGANISM: Artificial
<220> FEATURE:
<223> OTHER INFORMATION: Synthetic peptide

<400> SEQUENCE: 54

Gly Lys Lys Lys Lys Lys Gln Lys Lys Lys Lys Leu Ser Ser Ile Glu
1               5                   10                  15

Ser Asp Val

<210> SEQ ID NO 55
<211> LENGTH: 18
<212> TYPE: PRT
<213> ORGANISM: Artificial
<220> FEATURE:
<223> OTHER INFORMATION: Synthetic peptide

<400> SEQUENCE: 55

Arg Lys Lys Arg Arg Gln Arg Arg Arg Lys Leu Ser Ser Ile Glu Ser
1               5                   10                  15

Asp Val

<210> SEQ ID NO 56
<211> LENGTH: 19
<212> TYPE: PRT
<213> ORGANISM: Artificial
<220> FEATURE:
<223> OTHER INFORMATION: Synthetic peptide

<400> SEQUENCE: 56

Gly Ala Lys Lys Arg Arg Gln Arg Arg Arg Lys Leu Ser Ser Ile Glu
1               5                   10                  15

Ser Asp Val

<210> SEQ ID NO 57
<211> LENGTH: 18
<212> TYPE: PRT
<213> ORGANISM: Artificial
<220> FEATURE:
<223> OTHER INFORMATION: Synthetic peptide

<400> SEQUENCE: 57

Ala Lys Lys Arg Arg Gln Arg Arg Arg Lys Leu Ser Ser Ile Glu Ser
1               5                   10                  15

Asp Val

<210> SEQ ID NO 58
<211> LENGTH: 19
<212> TYPE: PRT
<213> ORGANISM: Artificial
<220> FEATURE:
<223> OTHER INFORMATION: Synthetic peptide
```

<400> SEQUENCE: 58

Gly Arg Lys Ala Arg Arg Gln Arg Arg Lys Leu Ser Ser Ile Glu
1               5                   10                  15

Ser Asp Val

<210> SEQ ID NO 59
<211> LENGTH: 18
<212> TYPE: PRT
<213> ORGANISM: Artificial
<220> FEATURE:
<223> OTHER INFORMATION: Synthetic peptide

<400> SEQUENCE: 59

Arg Lys Ala Arg Arg Gln Arg Arg Lys Leu Ser Ser Ile Glu Ser
1               5                   10                  15

Asp Val

<210> SEQ ID NO 60
<211> LENGTH: 19
<212> TYPE: PRT
<213> ORGANISM: Artificial
<220> FEATURE:
<223> OTHER INFORMATION: Synthetic peptide

<400> SEQUENCE: 60

Gly Arg Lys Lys Ala Arg Gln Arg Arg Lys Leu Ser Ser Ile Glu
1               5                   10                  15

Ser Asp Val

<210> SEQ ID NO 61
<211> LENGTH: 18
<212> TYPE: PRT
<213> ORGANISM: Artificial
<220> FEATURE:
<223> OTHER INFORMATION: Synthetic peptide

<400> SEQUENCE: 61

Arg Lys Lys Ala Arg Gln Arg Arg Lys Leu Ser Ser Ile Glu Ser
1               5                   10                  15

Asp Val

<210> SEQ ID NO 62
<211> LENGTH: 19
<212> TYPE: PRT
<213> ORGANISM: Artificial
<220> FEATURE:
<223> OTHER INFORMATION: Synthetic peptide

<400> SEQUENCE: 62

Gly Arg Lys Lys Arg Arg Gln Ala Arg Lys Leu Ser Ser Ile Glu
1               5                   10                  15

Ser Asp Val

<210> SEQ ID NO 63
<211> LENGTH: 18
<212> TYPE: PRT
<213> ORGANISM: Artificial
<220> FEATURE:
<223> OTHER INFORMATION: Synthetic peptide

<400> SEQUENCE: 63

Arg Lys Lys Arg Arg Gln Ala Arg Arg Lys Leu Ser Ser Ile Glu Ser

Asp Val

<210> SEQ ID NO 64
<211> LENGTH: 19
<212> TYPE: PRT
<213> ORGANISM: Artificial
<220> FEATURE:
<223> OTHER INFORMATION: Synthetic peptide

<400> SEQUENCE: 64

Gly Arg Lys Lys Arg Arg Gln Arg Ala Arg Lys Leu Ser Ser Ile Glu
1               5                   10                  15

Ser Asp Val

<210> SEQ ID NO 65
<211> LENGTH: 18
<212> TYPE: PRT
<213> ORGANISM: Artificial
<220> FEATURE:
<223> OTHER INFORMATION: Synthetic peptide

<400> SEQUENCE: 65

Arg Lys Lys Arg Arg Gln Arg Ala Arg Lys Leu Ser Ser Ile Glu Ser
1               5                   10                  15

Asp Val

<210> SEQ ID NO 66
<211> LENGTH: 20
<212> TYPE: PRT
<213> ORGANISM: Artificial
<220> FEATURE:
<223> OTHER INFORMATION: Synthetic peptide

<400> SEQUENCE: 66

Arg Arg Pro Arg Arg Pro Arg Arg Pro Arg Arg Lys Leu Ser Ser Ile
1               5                   10                  15

Glu Ser Asp Val
            20

<210> SEQ ID NO 67
<211> LENGTH: 20
<212> TYPE: PRT
<213> ORGANISM: Artificial
<220> FEATURE:
<223> OTHER INFORMATION: Synthetic peptide

<400> SEQUENCE: 67

Arg Arg Ala Arg Arg Ala Arg Arg Ala Arg Arg Lys Leu Ser Ser Ile
1               5                   10                  15

Glu Ser Asp Val
            20

<210> SEQ ID NO 68
<211> LENGTH: 19
<212> TYPE: PRT
<213> ORGANISM: Artificial
<220> FEATURE:
<223> OTHER INFORMATION: Synthetic peptide

<400> SEQUENCE: 68

Arg Arg Arg Ala Arg Arg Arg Ala Arg Arg Lys Leu Ser Ser Ile Glu
1               5                   10                  15

Ser Asp Val

<210> SEQ ID NO 69
<211> LENGTH: 19
<212> TYPE: PRT
<213> ORGANISM: Artificial
<220> FEATURE:
<223> OTHER INFORMATION: Synthetic peptide

<400> SEQUENCE: 69

Arg Arg Arg Pro Arg Arg Arg Pro Arg Arg Lys Leu Ser Ser Ile Glu
1               5                   10                  15

Ser Asp Val

<210> SEQ ID NO 70
<211> LENGTH: 17
<212> TYPE: PRT
<213> ORGANISM: Artificial
<220> FEATURE:
<223> OTHER INFORMATION: Synthetic peptide

<400> SEQUENCE: 70

Arg Arg Pro Arg Arg Pro Arg Arg Lys Leu Ser Ser Ile Glu Ser Asp
1               5                   10                  15

Val

<210> SEQ ID NO 71
<211> LENGTH: 17
<212> TYPE: PRT
<213> ORGANISM: Artificial
<220> FEATURE:
<223> OTHER INFORMATION: Synthetic peptide

<400> SEQUENCE: 71

Arg Arg Ala Arg Arg Ala Arg Arg Lys Leu Ser Ser Ile Glu Ser Asp
1               5                   10                  15

Val

<210> SEQ ID NO 72
<211> LENGTH: 26
<212> TYPE: PRT
<213> ORGANISM: Artificial
<220> FEATURE:
<223> OTHER INFORMATION: Synthetic N-type calcium channel inhibitor -
      Ziconotide

<400> SEQUENCE: 72

Cys Lys Gly Lys Gly Ala Lys Cys Ser Arg Leu Met Tyr Asp Cys Cys
1               5                   10                  15

Thr Gly Ser Cys Arg Ser Gly Lys Cys Gly
            20                  25

<210> SEQ ID NO 73
<211> LENGTH: 20
<212> TYPE: PRT
<213> ORGANISM: Artificial
<220> FEATURE:
<223> OTHER INFORMATION: Synthetic peptide variant 1974
<220> FEATURE:
<221> NAME/KEY: MOD_RES
<222> LOCATION: (20)..(20)
<223> OTHER INFORMATION: Xaa is 3-fluoro-L-Valine

<400> SEQUENCE: 73

Tyr Gly Arg Lys Lys Arg Arg Gln Arg Arg Arg Lys Leu Ser Ser Ile

-continued

```
1               5                   10                  15

Glu Ser Asp Xaa
            20

<210> SEQ ID NO 74
<211> LENGTH: 20
<212> TYPE: PRT
<213> ORGANISM: Artificial
<220> FEATURE:
<223> OTHER INFORMATION: Synthetic peptide variant 1975
<220> FEATURE:
<221> NAME/KEY: MOD_RES
<222> LOCATION: (20)..(20)
<223> OTHER INFORMATION: Xaa is Nva

<400> SEQUENCE: 74

Tyr Gly Arg Lys Lys Arg Arg Gln Arg Arg Lys Leu Ser Ser Ile
1               5                   10                  15

Glu Thr Asp Xaa
            20

<210> SEQ ID NO 75
<211> LENGTH: 20
<212> TYPE: PRT
<213> ORGANISM: Artificial
<220> FEATURE:
<223> OTHER INFORMATION: Synthetic peptide variant 1978
<220> FEATURE:
<221> NAME/KEY: MOD_RES
<222> LOCATION: (18)..(18)
<223> OTHER INFORMATION: Xaa is L-2-amino-3-ureidopropionic acid

<400> SEQUENCE: 75

Tyr Gly Arg Lys Lys Arg Arg Gln Arg Arg Lys Leu Ser Ser Ile
1               5                   10                  15

Glu Xaa Asp Val
            20

<210> SEQ ID NO 76
<211> LENGTH: 20
<212> TYPE: PRT
<213> ORGANISM: Artificial
<220> FEATURE:
<223> OTHER INFORMATION: Synthetic peptide variant 1980

<400> SEQUENCE: 76

Tyr Gly Arg Lys Lys Arg Arg Gln Arg Arg Lys Leu Ser Ser Ile
1               5                   10                  15

Glu Thr Ala Leu
            20

<210> SEQ ID NO 77
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is a Phe modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 77

Xaa Gly Arg Lys Lys Arg Arg Gln Arg Arg Lys Leu Ser Ser Ile
```

```
1               5                  10                 15

Glu Ser Asp Val
            20

<210> SEQ ID NO 78
<211> LENGTH: 21
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 78

Xaa Phe Gly Arg Lys Lys Arg Arg Gln Arg Arg Arg Lys Leu Ser Ser
1               5                  10                 15

Ile Glu Ser Asp Val
            20

<210> SEQ ID NO 79
<211> LENGTH: 21
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 79

Xaa Phe Gly Arg Lys Lys Arg Arg Gln Arg Arg Arg Lys Leu Ser Ser
1               5                  10                 15

Ile Glu Ser Asp Val
            20

<210> SEQ ID NO 80
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is a Gly modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 80

Xaa Lys Lys Lys Lys Lys Gln Lys Lys Lys Lys Leu Ser Ser Ile Glu
1               5                  10                 15

Ser Asp Val

<210> SEQ ID NO 81
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate
```

-continued

```
<400> SEQUENCE: 81

Xaa Gly Lys Lys Lys Lys Gln Lys Lys Lys Leu Ser Ser Ile
1               5                   10                  15

Glu Ser Asp Val
            20

<210> SEQ ID NO 82
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 82

Xaa Gly Lys Lys Lys Lys Gln Lys Lys Lys Leu Ser Ser Ile
1               5                   10                  15

Glu Ser Asp Val
            20

<210> SEQ ID NO 83
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an Arg modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 83

Xaa Lys Lys Arg Arg Gln Arg Arg Arg Lys Leu Ser Ser Ile Glu Ser
1               5                   10                  15

Asp Val

<210> SEQ ID NO 84
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 84

Xaa Arg Lys Lys Arg Arg Gln Arg Arg Arg Lys Leu Ser Ser Ile Glu
1               5                   10                  15

Ser Asp Val

<210> SEQ ID NO 85
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
```

<223> OTHER INFORMATION: Xaa is an amino acid other than Tyr

<400> SEQUENCE: 85

Xaa Arg Lys Lys Arg Arg Gln Arg Arg Arg Lys Leu Ser Ser Ile Glu
1               5                   10                  15

Ser Asp Val

<210> SEQ ID NO 86
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is a Gly modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 86

Xaa Ala Lys Lys Arg Arg Gln Arg Arg Arg Lys Leu Ser Ser Ile Glu
1               5                   10                  15

Ser Asp Val

<210> SEQ ID NO 87
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 87

Xaa Gly Ala Lys Lys Arg Arg Gln Arg Arg Arg Lys Leu Ser Ser Ile
1               5                   10                  15

Glu Ser Asp Val
            20

<210> SEQ ID NO 88
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other that tyrosine
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 88

Xaa Gly Ala Lys Lys Arg Arg Gln Arg Arg Arg Lys Leu Ser Ser Ile
1               5                   10                  15

Glu Ser Asp Val
            20

<210> SEQ ID NO 89
<211> LENGTH: 18
<212> TYPE: PRT

```
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is a Ala modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 89

Xaa Lys Lys Arg Arg Gln Arg Arg Arg Lys Leu Ser Ser Ile Glu Ser
1               5                   10                  15

Asp Val

<210> SEQ ID NO 90
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 90

Xaa Ala Lys Lys Arg Arg Gln Arg Arg Arg Lys Leu Ser Ser Ile Glu
1               5                   10                  15

Ser Asp Val

<210> SEQ ID NO 91
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 91

Xaa Ala Lys Lys Arg Arg Gln Arg Arg Arg Lys Leu Ser Ser Ile Glu
1               5                   10                  15

Ser Asp Val

<210> SEQ ID NO 92
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is a Gly modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 92

Xaa Arg Lys Ala Arg Arg Gln Arg Arg Arg Lys Leu Ser Ser Ile Glu
1               5                   10                  15

Ser Asp Val
```

```
<210> SEQ ID NO 93
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 93

Xaa Gly Arg Lys Ala Arg Arg Gln Arg Arg Lys Leu Ser Ser Ile
1               5                   10                  15

Glu Ser Asp Val
            20

<210> SEQ ID NO 94
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 94

Xaa Gly Arg Lys Ala Arg Arg Gln Arg Arg Lys Leu Ser Ser Ile
1               5                   10                  15

Glu Ser Asp Val
            20

<210> SEQ ID NO 95
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an Arg modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 95

Xaa Lys Ala Arg Arg Gln Arg Arg Lys Leu Ser Ser Ile Glu Ser
1               5                   10                  15

Asp Val

<210> SEQ ID NO 96
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 96

Xaa Arg Lys Ala Arg Arg Gln Arg Arg Lys Leu Ser Ser Ile Glu
1               5                   10                  15

Ser Asp Val
```

```
<210> SEQ ID NO 97
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 97

Xaa Arg Lys Ala Arg Arg Gln Arg Arg Arg Lys Leu Ser Ser Ile Glu
1               5                   10                  15

Ser Asp Val

<210> SEQ ID NO 98
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is a Gly modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 98

Xaa Arg Lys Lys Ala Arg Gln Arg Arg Arg Lys Leu Ser Ser Ile Glu
1               5                   10                  15

Ser Asp Val

<210> SEQ ID NO 99
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 99

Xaa Gly Arg Lys Lys Ala Arg Gln Arg Arg Lys Leu Ser Ser Ile
1               5                   10                  15

Glu Ser Asp Val
            20

<210> SEQ ID NO 100
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 100

Xaa Gly Arg Lys Lys Ala Arg Gln Arg Arg Arg Lys Leu Ser Ser Ile
1               5                   10                  15
```

Glu Ser Asp Val
            20

<210> SEQ ID NO 101
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an Arg modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 101

Xaa Lys Lys Ala Arg Gln Arg Arg Arg Lys Leu Ser Ser Ile Glu Ser
1               5                   10                  15

Asp Val

<210> SEQ ID NO 102
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 102

Xaa Arg Lys Lys Ala Arg Gln Arg Arg Arg Lys Leu Ser Ser Ile Glu
1               5                   10                  15

Ser Asp Val

<210> SEQ ID NO 103
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 103

Xaa Arg Lys Lys Ala Arg Gln Arg Arg Arg Lys Leu Ser Ser Ile Glu
1               5                   10                  15

Ser Asp Val

<210> SEQ ID NO 104
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is a Gly modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 104

```
Xaa Arg Lys Lys Arg Arg Gln Ala Arg Arg Lys Leu Ser Ser Ile Glu
1               5                   10                  15

Ser Asp Val

<210> SEQ ID NO 105
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 105

Xaa Gly Arg Lys Lys Arg Arg Gln Ala Arg Arg Lys Leu Ser Ser Ile
1               5                   10                  15

Glu Ser Asp Val
            20

<210> SEQ ID NO 106
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 106

Xaa Gly Arg Lys Lys Arg Arg Gln Ala Arg Arg Lys Leu Ser Ser Ile
1               5                   10                  15

Glu Ser Asp Val
            20

<210> SEQ ID NO 107
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an Arg modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 107

Xaa Lys Lys Arg Arg Gln Ala Arg Arg Lys Leu Ser Ser Ile Glu Ser
1               5                   10                  15

Asp Val

<210> SEQ ID NO 108
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate
```

```
<400> SEQUENCE: 108

Xaa Arg Lys Lys Arg Arg Gln Ala Arg Arg Lys Leu Ser Ser Ile Glu
1               5                   10                  15

Ser Asp Val

<210> SEQ ID NO 109
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 109

Xaa Arg Lys Lys Arg Arg Gln Ala Arg Arg Lys Leu Ser Ser Ile Glu
1               5                   10                  15

Ser Asp Val

<210> SEQ ID NO 110
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is a Gly modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 110

Xaa Arg Lys Lys Arg Arg Gln Arg Ala Arg Lys Leu Ser Ser Ile Glu
1               5                   10                  15

Ser Asp Val

<210> SEQ ID NO 111
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 111

Xaa Gly Arg Lys Lys Arg Arg Gln Arg Ala Arg Lys Leu Ser Ser Ile
1               5                   10                  15

Glu Ser Asp Val
            20

<210> SEQ ID NO 112
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
```

<223> OTHER INFORMATION: Xaa is an amino acid other than Tyr

<400> SEQUENCE: 112

Xaa Gly Arg Lys Lys Arg Arg Gln Arg Ala Arg Lys Leu Ser Ser Ile
1               5                   10                  15

Glu Ser Asp Val
            20

<210> SEQ ID NO 113
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an Arg modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 113

Xaa Lys Lys Arg Arg Gln Arg Ala Arg Lys Leu Ser Ser Ile Glu Ser
1               5                   10                  15

Asp Val

<210> SEQ ID NO 114
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 114

Xaa Arg Lys Lys Arg Arg Gln Arg Ala Arg Lys Leu Ser Ser Ile Glu
1               5                   10                  15

Ser Asp Val

<210> SEQ ID NO 115
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 115

Xaa Arg Lys Lys Arg Arg Gln Arg Ala Arg Lys Leu Ser Ser Ile Glu
1               5                   10                  15

Ser Asp Val

<210> SEQ ID NO 116
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE

```
<222> LOCATION: (1)..(1)
<223> OTHER INFORMATION: Xaa is an Arg modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 116

Xaa Arg Pro Arg Arg Pro Arg Arg Pro Arg Arg Lys Leu Ser Ser Ile
1               5                   10                  15

Glu Ser Asp Val
            20

<210> SEQ ID NO 117
<211> LENGTH: 21
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 117

Xaa Arg Arg Pro Arg Arg Pro Arg Arg Pro Arg Arg Lys Leu Ser Ser
1               5                   10                  15

Ile Glu Ser Asp Val
            20

<210> SEQ ID NO 118
<211> LENGTH: 21
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 118

Xaa Arg Arg Pro Arg Arg Pro Arg Arg Pro Arg Arg Lys Leu Ser Ser
1               5                   10                  15

Ile Glu Ser Asp Val
            20

<210> SEQ ID NO 119
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an Arg modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 119

Xaa Arg Ala Arg Arg Ala Arg Arg Ala Arg Arg Lys Leu Ser Ser Ile
1               5                   10                  15

Glu Ser Asp Val
            20

<210> SEQ ID NO 120
```

```
<211> LENGTH: 21
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 120

Xaa Arg Arg Ala Arg Arg Ala Arg Arg Ala Arg Arg Lys Leu Ser Ser
1               5                   10                  15

Ile Glu Ser Asp Val
            20

<210> SEQ ID NO 121
<211> LENGTH: 21
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 121

Xaa Arg Arg Ala Arg Arg Ala Arg Arg Ala Arg Arg Lys Leu Ser Ser
1               5                   10                  15

Ile Glu Ser Asp Val
            20

<210> SEQ ID NO 122
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an Arg modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 122

Xaa Arg Arg Ala Arg Arg Ala Arg Arg Lys Leu Ser Ser Ile Glu
1               5                   10                  15

Ser Asp Val

<210> SEQ ID NO 123
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 123

Xaa Arg Arg Arg Ala Arg Arg Ala Arg Arg Lys Leu Ser Ser Ile
1               5                   10                  15

Glu Ser Asp Val
            20
```

<210> SEQ ID NO 124
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 124

Xaa Arg Arg Arg Ala Arg Arg Arg Ala Arg Arg Lys Leu Ser Ser Ile
1               5                   10                  15

Glu Ser Asp Val
            20

<210> SEQ ID NO 125
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an Arg modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 125

Xaa Arg Arg Pro Arg Arg Arg Pro Arg Arg Lys Leu Ser Ser Ile Glu
1               5                   10                  15

Ser Asp Val

<210> SEQ ID NO 126
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 126

Xaa Arg Arg Arg Pro Arg Arg Arg Pro Arg Arg Lys Leu Ser Ser Ile
1               5                   10                  15

Glu Ser Asp Val
            20

<210> SEQ ID NO 127
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 127

Xaa Arg Arg Arg Pro Arg Arg Arg Pro Arg Arg Lys Leu Ser Ser Ile
1               5                   10                  15

Glu Ser Asp Val
            20

<210> SEQ ID NO 128
<211> LENGTH: 17
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an Arg modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 128

Xaa Arg Pro Arg Arg Pro Arg Arg Lys Leu Ser Ser Ile Glu Ser Asp
1               5                   10                  15

Val

<210> SEQ ID NO 129
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 129

Xaa Arg Arg Pro Arg Arg Pro Arg Arg Lys Leu Ser Ser Ile Glu Ser
1               5                   10                  15

Asp Val

<210> SEQ ID NO 130
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 130

Xaa Arg Arg Pro Arg Arg Pro Arg Arg Lys Leu Ser Ser Ile Glu Ser
1               5                   10                  15

Asp Val

<210> SEQ ID NO 131
<211> LENGTH: 17
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an Arg modified by a biotin molecule or
      other capping moiety including, but not limited to, H, acetyl,
      benzoyl, alkyl group (aliphatic), alkyl group with cycloalkyl
      group at the end, biotin with alkyl spacer, (5,6)-FAM.

<400> SEQUENCE: 131

Xaa Arg Ala Arg Arg Ala Arg Arg Lys Leu Ser Ser Ile Glu Ser Asp
1               5                   10                  15

Val

<210> SEQ ID NO 132
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pyroglutamate

<400> SEQUENCE: 132

Xaa Arg Arg Ala Arg Arg Ala Arg Arg Lys Leu Ser Ser Ile Glu Ser
1               5                   10                  15

Asp Val

<210> SEQ ID NO 133
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid other than Tyr

<400> SEQUENCE: 133

Xaa Arg Arg Ala Arg Arg Ala Arg Arg Lys Leu Ser Ser Ile Glu Ser
1               5                   10                  15

Asp Val

<210> SEQ ID NO 134
<211> LENGTH: 5
<212> TYPE: PRT
<213> ORGANISM: Artificial
<220> FEATURE:
<223> OTHER INFORMATION: Synthetic peptide

<400> SEQUENCE: 134

Gly Ser Ser Ser Ser
1               5

<210> SEQ ID NO 135
<211> LENGTH: 11
<212> TYPE: PRT
<213> ORGANISM: Artificial
<220> FEATURE:
<223> OTHER INFORMATION: Synthetic internalization peptide

<400> SEQUENCE: 135

Phe Gly Arg Lys Lys Arg Arg Gln Arg Arg Arg
1               5                   10

<210> SEQ ID NO 136
<211> LENGTH: 10
<212> TYPE: PRT
<213> ORGANISM: Artificial
<220> FEATURE:
<223> OTHER INFORMATION: Synthetic internalization peptide -continued

```
<400> SEQUENCE: 136

Gly Arg Lys Lys Arg Arg Gln Arg Arg Arg
1               5                   10
```